US010543064B2

(12) United States Patent
Kuo

(10) Patent No.: US 10,543,064 B2
(45) Date of Patent: Jan. 28, 2020

(54) DENTAL IMPLANT POSITIONING

(71) Applicant: Align Technology, Inc., San Jose, CA (US)

(72) Inventor: Eric E. Kuo, San Jose, CA (US)

(73) Assignee: Align Technology, Inc., San Jose, CA (US)

(*) Notice: Subject to any disclaimer, the term of this patent is extended or adjusted under 35 U.S.C. 154(b) by 0 days.

(21) Appl. No.: 15/341,828

(22) Filed: Nov. 2, 2016

(65) Prior Publication Data

US 2017/0071705 A1     Mar. 16, 2017

Related U.S. Application Data

(63) Continuation of application No. 12/154,526, filed on May 23, 2008, now Pat. No. 9,492,243.

(51) Int. Cl.
*A61C 8/00* (2006.01)
*A61C 7/08* (2006.01)
(Continued)

(52) U.S. Cl.
CPC .............. *A61C 8/0096* (2013.01); *A61B 6/12* (2013.01); *A61B 6/145* (2013.01); *A61C 1/084* (2013.01);
(Continued)

(58) Field of Classification Search
CPC ..... A61C 8/0096; A61C 8/0089; A61C 8/008; A61C 1/084; A61C 7/08; A61C 13/0001;
(Continued)

(56) References Cited

U.S. PATENT DOCUMENTS 2,171,695 A     9/1939   Harper
2,194,790 A     3/1940   Gluck
(Continued)

FOREIGN PATENT DOCUMENTS

AU     517102 B     11/1977
AU    3031677 A     11/1977
(Continued)

OTHER PUBLICATIONS

Wong et al., "Computer-aided design/computer-aided manufacturing surgical guidance for placement of dental implants: Case report," Implant Dentistry, Sep. 2007 16(3): 123-30.
(Continued)

*Primary Examiner* — Matthew M Nelson
(74) *Attorney, Agent, or Firm* — Shay Glenn LLP

(57) ABSTRACT

Methods, devices, systems, and series of appliances are provided for dental implant positioning. One method for positioning an implant with dental treatment includes determining an implant location based on a virtual model of an optimized dental occlusion, moving one or more teeth using a first number of a series of dental appliances, from a first orientation to a second orientation, the second orientation exposing the implant location, placing an implant at the exposed implant location using a landmark included in at least one of the series of dental appliances, repositioning one or more teeth using a second number of the series of dental appliances, from the second orientation to a successive orientation.

27 Claims, 8 Drawing Sheets

(51) Int. Cl.
*A61C 1/08* (2006.01)
*A61B 6/12* (2006.01)
*A61B 6/14* (2006.01)
A61C 13/107 (2006.01)
A61B 90/00 (2016.01)

(52) U.S. Cl.
CPC .............. *A61C 7/08* (2013.01); *A61C 8/008* (2013.01); *A61C 8/0089* (2013.01); *A61B 2090/395* (2016.02); *A61B 2090/3912* (2016.02); *A61B 2090/3916* (2016.02); *A61B 2090/3966* (2016.02); *A61B 2090/3983* (2016.02); *A61B 2090/3991* (2016.02); *A61C 13/0001* (2013.01)

(58) Field of Classification Search
CPC ... A61B 6/145; A61B 6/12; A61B 2090/3912; A61B 2090/3991; A61B 2090/395; A61B 2090/2983; A61B 2090/3916; A61B 2090/3966
USPC .......................................................... 433/24
See application file for complete search history.

(56) References Cited

U.S. PATENT DOCUMENTS

| | | |
|---|---|---|
| 2,467,432 A | 4/1949 | Kesling |
| 2,531,222 A | 11/1950 | Kesling |
| 2,835,628 A | 5/1958 | Saffir |
| 3,089,487 A | 5/1963 | Enicks et al. |
| 3,092,907 A | 6/1963 | Traiger |
| 3,178,820 A | 4/1965 | Kesling |
| 3,211,143 A | 10/1965 | Grossberg |
| 3,379,193 A | 4/1968 | Monsghan |
| 3,385,291 A | 5/1968 | Martin |
| 3,407,500 A | 10/1968 | Kesling |
| 3,478,742 A | 11/1969 | Bohlmann |
| 3,496,936 A | 2/1970 | Gores |
| 3,503,127 A | 3/1970 | Kasdin et al. |
| 3,533,163 A | 10/1970 | Kirschenbaum |
| 3,556,093 A | 1/1971 | Quick |
| 3,600,808 A | 8/1971 | Reeve |
| 3,660,900 A | 5/1972 | Andrews |
| 3,683,502 A | 8/1972 | Wallshein |
| 3,724,075 A | 4/1973 | Kesling |
| 3,738,005 A | 6/1973 | Cohen et al. |
| 3,797,115 A | 3/1974 | Silverman et al. |
| 3,813,781 A | 6/1974 | Forgione |
| 3,860,803 A | 1/1975 | Levine |
| 3,885,310 A | 5/1975 | Northcutt |
| 3,916,526 A | 11/1975 | Schudy |
| 3,922,786 A | 12/1975 | Lavin |
| 3,949,477 A | 4/1976 | Cohen et al. |
| 3,950,851 A | 4/1976 | Bergersen |
| 3,955,282 A | 5/1976 | McNall |
| 3,983,628 A | 10/1976 | Acevedo |
| 4,014,096 A | 3/1977 | Dellinger |
| 4,039,653 A | 8/1977 | DeFoney et al. |
| 4,055,895 A | 11/1977 | Huge |
| 4,094,068 A | 6/1978 | Schinhammer |
| 4,117,596 A | 10/1978 | Wallshein |
| 4,129,946 A | 12/1978 | Kennedy |
| 4,134,208 A | 1/1979 | Pearlman |
| 4,139,944 A | 2/1979 | Bergersen |
| 4,179,811 A | 12/1979 | Hinz |
| 4,179,812 A | 12/1979 | White |
| 4,183,141 A | 1/1980 | Dellinger |
| 4,195,046 A | 3/1980 | Kesling |
| 4,204,325 A | 5/1980 | Kaelble |
| 4,253,828 A | 3/1981 | Coles et al. |
| 4,255,138 A | 3/1981 | Frohn |
| 4,278,087 A | 7/1981 | Theeuwes |
| 4,299,568 A | 11/1981 | Crowley |
| 4,324,546 A | 4/1982 | Heitlinger et al. |
| 4,324,547 A | 4/1982 | Arcan et al. |
| 4,348,178 A | 9/1982 | Kurz |
| 4,368,040 A | 1/1983 | Weissman |
| 4,419,992 A | 12/1983 | Chorbajian |
| 4,433,956 A | 2/1984 | Witzig |
| 4,433,960 A | 2/1984 | Garito et al. |
| 4,439,154 A | 3/1984 | Mayclin |
| 4,449,928 A | 5/1984 | von Weissenfluh |
| 4,450,150 A | 5/1984 | Sidman |
| 4,478,580 A | 10/1984 | Barrut |
| 4,500,294 A | 2/1985 | Lewis |
| 4,505,672 A | 3/1985 | Kurz |
| 4,505,673 A | 3/1985 | Yoshii |
| 4,519,386 A | 5/1985 | Sullivan |
| 4,523,908 A | 6/1985 | Drisaldi et al. |
| 4,526,540 A | 7/1985 | Dellinger |
| 4,553,936 A | 11/1985 | Wang |
| 4,575,330 A | 3/1986 | Hull |
| 4,575,805 A | 3/1986 | Moermann et al. |
| 4,591,341 A | 5/1986 | Andrews |
| 4,608,021 A | 8/1986 | Barrett |
| 4,609,349 A | 9/1986 | Cain |
| 4,611,288 A | 9/1986 | Duret et al. |
| 4,629,424 A | 12/1986 | Lauks et al. |
| 4,638,145 A | 1/1987 | Sakuma et al. |
| 4,656,860 A | 4/1987 | Orthuber et al. |
| 4,663,720 A | 5/1987 | Duret et al. |
| 4,664,626 A | 5/1987 | Kesling |
| 4,665,621 A | 5/1987 | Ackerman et al. |
| 4,676,747 A | 6/1987 | Kesling |
| 4,741,700 A | 5/1988 | Barabe |
| 4,755,139 A | 7/1988 | Abbatte et al. |
| 4,757,824 A | 7/1988 | Chaumet |
| 4,763,791 A | 8/1988 | Halverson et al. |
| 4,764,111 A | 8/1988 | Knierim |
| 4,790,752 A | 12/1988 | Cheslak |
| 4,793,803 A | 12/1988 | Martz |
| 4,798,534 A | 1/1989 | Breads |
| 4,818,542 A | 4/1989 | De Luca et al. |
| 4,830,612 A | 5/1989 | Bergersen |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,861,268 A | 8/1989 | Garay et al. |
| 4,877,398 A | 10/1989 | Kesling |
| 4,880,380 A | 11/1989 | Martz |
| 4,886,451 A | 12/1989 | Cetlin |
| 4,889,238 A | 12/1989 | Batchelor |
| 4,890,608 A | 1/1990 | Steer |
| 4,932,866 A | 6/1990 | Guis |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,952,928 A | 8/1990 | Carroll et al. |
| 4,964,770 A | 10/1990 | Steinbichler et al. |
| 4,968,251 A | 11/1990 | Darnell |
| 4,971,557 A | 11/1990 | Martin |
| 4,975,052 A | 12/1990 | Spencer et al. |
| 4,983,334 A | 1/1991 | Adell |
| 4,997,369 A | 3/1991 | Shafir |
| 5,002,485 A | 3/1991 | Aagesen |
| 5,011,405 A | 4/1991 | Lemchen |
| 5,015,183 A * | 5/1991 | Fenick ..................... A61B 6/14 433/173 |
| 5,017,133 A | 5/1991 | Miura |
| 5,018,969 A | 5/1991 | Andreiko et al. |
| 5,027,281 A | 6/1991 | Rekow et al. |
| 5,035,613 A | 7/1991 | Breads et al. |
| 5,037,295 A | 8/1991 | Bergersen |
| 5,049,077 A | 9/1991 | Goldin et al. |
| 5,055,039 A | 10/1991 | Abbatte et al. |
| 5,061,839 A | 10/1991 | Matsuno et al. |
| 5,083,919 A | 1/1992 | Quachi |
| 5,094,614 A | 3/1992 | Wildman |
| 5,100,316 A | 3/1992 | Wildman |
| 5,103,838 A | 4/1992 | Yousif |

(56) References Cited

U.S. PATENT DOCUMENTS

| | | |
|---|---|---|
| 5,114,339 A | 5/1992 | Guis |
| 5,121,333 A | 6/1992 | Riley et al. |
| 5,123,425 A | 6/1992 | Shannon et al. |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,194,003 A | 3/1993 | Garay et al. |
| 5,204,670 A | 4/1993 | Stinton |
| 5,222,499 A | 6/1993 | Allen et al. |
| 5,224,049 A | 6/1993 | Mushabac |
| 5,238,404 A | 8/1993 | Andreiko |
| 5,242,304 A | 9/1993 | Truax et al. |
| 5,245,592 A | 9/1993 | Kuemmel et al. |
| 5,273,429 A | 12/1993 | Rekow et al. |
| 5,278,756 A | 1/1994 | Lemchen et al. |
| 5,306,144 A | 4/1994 | Hibst et al. |
| 5,314,335 A | 5/1994 | Fung |
| 5,324,186 A | 6/1994 | Bakanowski |
| 5,328,362 A | 7/1994 | Watson et al. |
| 5,335,657 A | 8/1994 | Terry et al. |
| 5,338,198 A | 8/1994 | Wu et al. |
| 5,340,309 A | 8/1994 | Robertson |
| 5,342,202 A | 8/1994 | Deshayes |
| 5,344,315 A | 9/1994 | Hanson |
| 5,368,478 A | 11/1994 | Andreiko et al. |
| 5,372,502 A | 12/1994 | Massen et al. |
| D354,355 S | 1/1995 | Hilgers |
| 5,382,164 A | 1/1995 | Stern |
| 5,395,238 A | 3/1995 | Andreiko et al. |
| 5,415,542 A | 5/1995 | Kesling |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,449,703 A | 9/1995 | Mitra et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| 5,487,662 A | 1/1996 | Kipke et al. |
| RE35,169 E | 3/1996 | Lemchen et al. |
| 5,499,633 A | 3/1996 | Fenton |
| 5,522,725 A | 6/1996 | Jordan et al. |
| 5,528,735 A | 6/1996 | Strasnick et al. |
| 5,533,895 A | 7/1996 | Andreiko et al. |
| 5,540,732 A | 7/1996 | Testerman |
| 5,542,842 A | 8/1996 | Andreiko et al. |
| 5,543,780 A | 8/1996 | McAuley et al. |
| 5,549,476 A | 8/1996 | Stern |
| 5,562,448 A | 10/1996 | Mushabac |
| 5,570,182 A | 10/1996 | Nathel et al. |
| 5,575,655 A | 11/1996 | Darnell |
| 5,583,977 A | 12/1996 | Seidl |
| 5,587,912 A | 12/1996 | Andersson et al. |
| 5,588,098 A | 12/1996 | Chen et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,626,537 A | 5/1997 | Danyo et al. |
| 5,636,736 A | 6/1997 | Jacobs et al. |
| 5,645,420 A | 7/1997 | Bergersen |
| 5,645,421 A | 7/1997 | Slootsky |
| 5,651,671 A | 7/1997 | Seay et al. |
| 5,655,653 A | 8/1997 | Chester |
| 5,659,420 A | 8/1997 | Wakai et al. |
| 5,683,243 A | 11/1997 | Andreiko et al. |
| 5,683,244 A | 11/1997 | Truax |
| 5,691,539 A | 11/1997 | Pfeiffer |
| 5,692,894 A | 12/1997 | Schwartz et al. |
| 5,711,665 A | 1/1998 | Adam et al. |
| 5,711,666 A | 1/1998 | Hanson |
| 5,725,376 A | 3/1998 | Poirier |
| 5,725,378 A | 3/1998 | Wang |
| 5,730,151 A | 3/1998 | Summer et al. |
| 5,737,084 A | 4/1998 | Ishihara |
| 5,740,267 A | 4/1998 | Echerer et al. |
| 5,742,700 A | 4/1998 | Yoon et al. |
| 5,769,631 A | 6/1998 | Williams |
| 5,774,425 A | 6/1998 | Ivanov et al. |
| 5,790,242 A | 8/1998 | Stern et al. |
| 5,799,100 A | 8/1998 | Clarke et al. |
| 5,800,162 A | 9/1998 | Shimodaira et al. |
| 5,800,174 A | 9/1998 | Andersson |
| 5,813,854 A | 9/1998 | Nikodem |
| 5,816,800 A | 10/1998 | Brehm et al. |
| 5,818,587 A | 10/1998 | Devaraj et al. |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,876,199 A | 3/1999 | Bergersen |
| 5,879,158 A | 3/1999 | Doyle et al. |
| 5,880,961 A | 3/1999 | Crump |
| 5,880,962 A | 3/1999 | Andersson et al. |
| 5,882,192 A | 3/1999 | Bergersen |
| 5,886,702 A | 3/1999 | Migdal et al. |
| 5,890,896 A | 4/1999 | Padial |
| 5,904,479 A | 5/1999 | Staples |
| 5,911,576 A | 6/1999 | Ulrich et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A * | 11/1999 | Chishti .................. A61C 7/00 |
| 5,975,906 A | 11/1999 | Knutson |
| 5,980,246 A | 11/1999 | Ramsay et al. |
| 5,989,023 A | 11/1999 | Summer et al. |
| 5,993,413 A | 11/1999 | Aaltonen et al. |
| 6,002,706 A | 12/1999 | Staver et al. |
| 6,018,713 A | 1/2000 | Coli et al. |
| 6,044,309 A | 3/2000 | Honda |
| 6,049,743 A | 4/2000 | Baba |
| 6,053,731 A | 4/2000 | Heckenberger |
| 6,068,482 A | 5/2000 | Snow |
| 6,070,140 A | 5/2000 | Tran |
| 6,099,303 A | 8/2000 | Gibbs et al. |
| 6,099,314 A | 8/2000 | Kopelman et al. |
| 6,102,701 A | 8/2000 | Engeron |
| 6,120,287 A | 9/2000 | Chen |
| 6,123,544 A | 9/2000 | Cleary |
| 6,152,731 A | 11/2000 | Jordan et al. |
| 6,154,676 A | 11/2000 | Levine |
| 6,183,248 B1 | 2/2001 | Chishti et al. |
| 6,183,249 B1 | 2/2001 | Brennan et al. |
| 6,186,780 B1 | 2/2001 | Hibst et al. |
| 6,190,165 B1 | 2/2001 | Andreiko et al. |
| 6,200,133 B1 | 3/2001 | Kittelsen |
| 6,201,880 B1 | 3/2001 | Elbaum et al. |
| 6,210,162 B1 | 4/2001 | Chishti et al. |
| 6,212,435 B1 | 4/2001 | Lattner et al. |
| 6,213,767 B1 | 4/2001 | Dixon et al. |
| 6,217,334 B1 | 4/2001 | Hultgren |
| 6,227,850 B1 | 5/2001 | Chishti et al. |
| 6,230,142 B1 | 5/2001 | Benigno et al. |
| 6,231,338 B1 | 5/2001 | de Josselin de Jong et al. |
| 6,239,705 B1 | 5/2001 | Glen |
| 6,243,601 B1 | 6/2001 | Wist |
| 6,263,234 B1 | 7/2001 | Engelhardt et al. |
| 6,283,761 B1 | 9/2001 | Joao |
| 6,288,138 B1 | 9/2001 | Yamamoto |
| 6,299,438 B1 | 10/2001 | Sahagian et al. |
| 6,309,215 B1 | 10/2001 | Phan et al. |
| 6,313,432 B1 | 11/2001 | Nagata et al. |
| 6,315,553 B1 | 11/2001 | Sachdeva et al. |
| 6,328,745 B1 | 12/2001 | Ascherman |
| 6,332,774 B1 | 12/2001 | Chikami |
| 6,334,073 B1 | 12/2001 | Levine |
| 6,350,120 B1 | 2/2002 | Sachdeva et al. |
| 6,364,660 B1 | 4/2002 | Durbin et al. |

(56) References Cited

U.S. PATENT DOCUMENTS

| | | | |
|---|---|---|---|
| 6,382,975 B1 | 5/2002 | Poirier |
| 6,386,878 B1 | 5/2002 | Pavlovskaia et al. |
| 6,394,802 B1 | 5/2002 | Hahn |
| 6,402,510 B1 | 6/2002 | Williams |
| 6,402,707 B1 | 6/2002 | Ernst |
| 6,405,729 B1 | 6/2002 | Thornton |
| 6,406,292 B1 | 6/2002 | Chishti et al. |
| 6,409,504 B1 | 6/2002 | Jones et al. |
| 6,413,086 B1 | 7/2002 | Womack |
| 6,414,264 B1 | 7/2002 | von Falkenhausen |
| 6,414,708 B1 | 7/2002 | Carmeli et al. |
| 6,435,871 B1 | 8/2002 | Inman |
| 6,436,058 B1 | 8/2002 | Krahner et al. |
| 6,441,354 B1 | 8/2002 | Seghatol et al. |
| 6,450,167 B1 | 9/2002 | David et al. |
| 6,450,807 B1 | 9/2002 | Chishti et al. |
| 6,462,301 B1 | 10/2002 | Scott et al. |
| 6,470,338 B1 | 10/2002 | Rizzo et al. |
| 6,471,511 B1 | 10/2002 | Chishti et al. |
| 6,471,512 B1 | 10/2002 | Sachdeva et al. |
| 6,471,970 B1 | 10/2002 | Fanara et al. |
| 6,482,002 B2 | 11/2002 | Jordan et al. |
| 6,482,298 B1 | 11/2002 | Bhatnagar |
| 6,496,814 B1 | 12/2002 | Busche |
| 6,496,816 B1 | 12/2002 | Thiesson et al. |
| 6,499,026 B1 | 12/2002 | Rivette et al. |
| 6,499,995 B1 | 12/2002 | Schwartz |
| 6,507,832 B1 | 1/2003 | Evans et al. |
| 6,514,074 B1 | 2/2003 | Chishti et al. |
| 6,515,593 B1 | 2/2003 | Stark et al. |
| 6,516,288 B2 | 2/2003 | Bagne |
| 6,516,805 B1 | 2/2003 | Thornton |
| 6,520,772 B2 | 2/2003 | Williams |
| 6,523,009 B1 | 2/2003 | Wilkins |
| 6,523,019 B1 | 2/2003 | Borthwick |
| 6,524,101 B1 | 2/2003 | Phan et al. |
| 6,526,168 B1 | 2/2003 | Ornes et al. |
| 6,526,982 B1 | 3/2003 | Strong |
| 6,529,891 B1 | 3/2003 | Heckerman |
| 6,529,902 B1 | 3/2003 | Kanevsky et al. |
| 6,532,455 B1 | 3/2003 | Martin et al. |
| 6,535,865 B1 | 3/2003 | Skaaning et al. |
| 6,540,512 B1 | 4/2003 | Sachdeva et al. |
| 6,540,707 B1 | 4/2003 | Stark et al. |
| 6,542,593 B1 | 4/2003 | Bowman Amuah |
| 6,542,881 B1 | 4/2003 | Meidan et al. |
| 6,542,894 B1 | 4/2003 | Lee et al. |
| 6,542,903 B2 | 4/2003 | Hull et al. |
| 6,551,243 B2 | 4/2003 | Bocionek et al. |
| 6,554,837 B1 * | 4/2003 | Hauri | A61B 17/154 606/87 |
| 6,556,659 B1 | 4/2003 | Bowman Amuah |
| 6,556,977 B1 | 4/2003 | Lapointe et al. |
| 6,560,592 B1 | 5/2003 | Reid et al. |
| 6,564,209 B1 | 5/2003 | Dempski et al. |
| 6,567,814 B1 | 5/2003 | Bankier et al. |
| 6,571,227 B1 | 5/2003 | Agrafiotis et al. |
| 6,572,372 B1 | 6/2003 | Phan et al. |
| 6,573,998 B2 | 6/2003 | Cohen Sabban |
| 6,574,561 B2 | 6/2003 | Alexander et al. |
| 6,578,003 B1 | 6/2003 | Camarda et al. |
| 6,580,948 B2 | 6/2003 | Haupert et al. |
| 6,587,529 B1 | 7/2003 | Staszewski et al. |
| 6,587,828 B1 | 7/2003 | Sachdeva |
| 6,592,368 B1 * | 7/2003 | Weathers, Jr. | A61B 17/176 433/76 |
| 6,594,539 B1 | 7/2003 | Geng |
| 6,595,342 B1 | 7/2003 | Maritzen et al. |
| 6,597,934 B1 | 7/2003 | de Jong et al. |
| 6,598,043 B1 | 7/2003 | Baclawski |
| 6,599,250 B2 | 7/2003 | Webb et al. |
| 6,602,070 B2 | 8/2003 | Miller et al. |
| 6,604,527 B1 | 8/2003 | Palmisano |
| 6,606,744 B1 | 8/2003 | Mikurak |
| 6,607,382 B1 | 8/2003 | Kuo et al. |
| 6,611,783 B2 | 8/2003 | Kelly et al. |
| 6,611,867 B1 | 8/2003 | Bowman Amuah |
| 6,613,001 B1 | 9/2003 | Dworkin |
| 6,615,158 B2 | 9/2003 | Wenzel et al. |
| 6,616,447 B1 | 9/2003 | Rizoiu et al. |
| 6,616,579 B1 | 9/2003 | Reinhold et al. |
| 6,621,491 B1 | 9/2003 | Baumrind et al. |
| 6,623,698 B2 | 9/2003 | Kuo |
| 6,624,752 B2 | 9/2003 | Klitsgaard et al. |
| 6,626,180 B1 | 9/2003 | Kittelsen et al. |
| 6,626,569 B2 | 9/2003 | Reinstein et al. |
| 6,626,669 B2 | 9/2003 | Zegarelli |
| 6,633,772 B2 | 10/2003 | Ford et al. |
| 6,640,128 B2 | 10/2003 | Vilsmeier et al. |
| 6,643,646 B2 | 11/2003 | Su et al. |
| 6,647,383 B1 | 11/2003 | August et al. |
| 6,650,944 B2 | 11/2003 | Goedeke et al. |
| 6,671,818 B1 | 12/2003 | Mikurak |
| 6,675,104 B2 | 1/2004 | Paulse et al. |
| 6,678,669 B2 | 1/2004 | Lapointe et al. |
| 6,682,346 B2 | 1/2004 | Chishti et al. |
| 6,685,469 B2 | 2/2004 | Chishti et al. |
| 6,689,055 B1 | 2/2004 | Mullen et al. |
| 6,690,761 B2 | 2/2004 | Lang et al. |
| 6,691,110 B2 | 2/2004 | Wang et al. |
| 6,694,234 B2 | 2/2004 | Lockwood et al. |
| 6,697,164 B1 | 2/2004 | Babayoff et al. |
| 6,697,793 B2 | 2/2004 | McGreevy |
| 6,702,575 B2 * | 3/2004 | Hilliard | A61C 7/00 433/18 |
| 6,702,765 B2 | 3/2004 | Robbins et al. |
| 6,702,804 B1 | 3/2004 | Ritter et al. |
| 6,705,863 B2 | 3/2004 | Phan et al. |
| 6,729,876 B2 | 5/2004 | Chishti et al. |
| 6,733,289 B2 | 5/2004 | Manemann et al. |
| 6,736,638 B1 | 5/2004 | Sachdeva et al. |
| 6,739,869 B1 | 5/2004 | Taub et al. |
| 6,744,932 B1 | 6/2004 | Rubbert et al. |
| 6,749,414 B1 | 6/2004 | Hanson et al. |
| 6,769,913 B2 | 8/2004 | Hurson |
| 6,772,026 B2 | 8/2004 | Bradbury et al. |
| 6,790,036 B2 | 9/2004 | Graham |
| 6,802,713 B1 | 10/2004 | Chishti et al. |
| 6,814,574 B2 | 11/2004 | Abolfathi et al. |
| 6,830,450 B2 | 12/2004 | Knopp et al. |
| 6,832,912 B2 | 12/2004 | Mao |
| 6,832,914 B1 | 12/2004 | Bonnet et al. |
| 6,843,370 B2 | 1/2005 | Tuneberg |
| 6,845,175 B2 | 1/2005 | Kopelman et al. |
| 6,885,464 B1 | 4/2005 | Pfeiffer et al. |
| 6,890,285 B2 | 5/2005 | Rahman et al. |
| 6,951,254 B2 | 10/2005 | Morrison |
| 6,976,841 B1 | 12/2005 | Osterwalder |
| 6,978,268 B2 | 12/2005 | Thomas et al. |
| 6,983,752 B2 | 1/2006 | Garabadian |
| 6,984,128 B2 | 1/2006 | Breining et al. |
| 6,988,893 B2 | 1/2006 | Haywood |
| 7,016,952 B2 | 3/2006 | Mullen et al. |
| 7,020,963 B2 | 4/2006 | Cleary et al. |
| 7,036,514 B2 | 5/2006 | Heck |
| 7,040,896 B2 | 5/2006 | Pavlovskaia et al. |
| 7,106,233 B2 | 9/2006 | Schroeder et al. |
| 7,112,065 B2 | 9/2006 | Kopelman et al. |
| 7,121,825 B2 | 10/2006 | Chishti et al. |
| 7,134,874 B2 | 11/2006 | Chishti et al. |
| 7,137,812 B2 | 11/2006 | Cleary et al. |
| 7,138,640 B1 | 11/2006 | Delgado et al. |
| 7,140,877 B2 | 11/2006 | Kaza |
| 7,142,312 B2 | 11/2006 | Quadling et al. |
| 7,155,373 B2 | 12/2006 | Jordan et al. |
| 7,156,655 B2 | 1/2007 | Sachdeva et al. |
| 7,156,661 B2 | 1/2007 | Choi et al. |
| 7,166,063 B2 | 1/2007 | Rahman et al. |
| 7,184,150 B2 | 2/2007 | Quadling et al. |
| 7,191,451 B2 | 3/2007 | Nakagawa |
| 7,192,273 B2 | 3/2007 | McSurdy |
| 7,194,781 B1 | 3/2007 | Orjela |
| 7,217,131 B2 | 5/2007 | Vuillemot |
| 7,220,122 B2 | 5/2007 | Chishti |

(56) References Cited

U.S. PATENT DOCUMENTS

| | | |
|---|---|---|
| 7,220,124 B2 | 5/2007 | Taub et al. |
| 7,229,282 B2 | 6/2007 | Andreiko et al. |
| 7,234,937 B2 | 6/2007 | Sachdeva et al. |
| 7,241,142 B2 | 7/2007 | Abolfathi et al. |
| 7,244,230 B2 | 7/2007 | Duggirala et al. |
| 7,245,753 B2 | 7/2007 | Squilla et al. |
| 7,257,136 B2 | 8/2007 | Mori et al. |
| 7,286,954 B2 | 10/2007 | Kopelman et al. |
| 7,292,759 B2 | 11/2007 | Boutoussov et al. |
| 7,294,141 B2 | 11/2007 | Bergersen |
| 7,302,842 B2 | 12/2007 | Biester et al. |
| 7,320,592 B2 | 1/2008 | Chishti et al. |
| 7,328,706 B2 | 2/2008 | Barach et al. |
| 7,329,122 B1 | 2/2008 | Scott |
| 7,338,327 B2 | 3/2008 | Sticker et al. |
| D565,509 S | 4/2008 | Fechner et al. |
| 7,351,116 B2 | 4/2008 | Dold |
| 7,354,270 B2 | 4/2008 | Abolfathi et al. |
| 7,357,637 B2 | 4/2008 | Liechtung |
| 7,435,083 B2 | 10/2008 | Chishti et al. |
| 7,450,231 B2 | 11/2008 | Johs et al. |
| 7,458,810 B2 | 12/2008 | Bergersen |
| 7,460,230 B2 | 12/2008 | Johs et al. |
| 7,462,076 B2 | 12/2008 | Walter et al. |
| 7,463,929 B2 | 12/2008 | Simmons |
| 7,476,100 B2 | 1/2009 | Kuo |
| 7,500,851 B2 | 3/2009 | Williams |
| D594,413 S | 6/2009 | Palka et al. |
| 7,543,511 B2 | 6/2009 | Kimura et al. |
| 7,544,103 B2 | 6/2009 | Walter et al. |
| 7,553,157 B2 | 6/2009 | Abolfathi et al. |
| 7,561,273 B2 | 7/2009 | Stautmeister et al. |
| 7,577,284 B2 | 8/2009 | Wong et al. |
| 7,596,253 B2 | 9/2009 | Wong et al. |
| 7,597,594 B2 | 10/2009 | Stadler et al. |
| 7,609,875 B2 | 10/2009 | Liu et al. |
| D603,796 S | 11/2009 | Sticker et al. |
| 7,616,319 B1 | 11/2009 | Woollam et al. |
| 7,626,705 B2 | 12/2009 | Altendorf |
| 7,632,216 B2 | 12/2009 | Rahman et al. |
| 7,633,625 B1 | 12/2009 | Woollam et al. |
| 7,637,262 B2 | 12/2009 | Bailey |
| 7,637,740 B2 | 12/2009 | Knopp |
| 7,641,473 B2 | 1/2010 | Sporbert et al. |
| 7,668,355 B2 | 2/2010 | Wong et al. |
| 7,670,179 B2 | 3/2010 | Müller |
| 7,695,327 B2 | 4/2010 | Bäuerle et al. |
| 7,698,068 B2 | 4/2010 | Babayoff |
| 7,711,447 B2 | 5/2010 | Lu et al. |
| 7,724,378 B2 | 5/2010 | Babayoff |
| D618,619 S | 6/2010 | Walter |
| 7,728,848 B2 | 6/2010 | Petrov et al. |
| 7,731,508 B2 | 6/2010 | Borst |
| 7,735,217 B2 | 6/2010 | Borst |
| 7,740,476 B2 | 6/2010 | Rubbert et al. |
| 7,744,369 B2 | 6/2010 | Imgrund et al. |
| 7,746,339 B2 | 6/2010 | Matov et al. |
| 7,780,460 B2 | 8/2010 | Walter |
| 7,787,132 B2 | 8/2010 | Körner et al. |
| 7,791,810 B2 | 9/2010 | Powell |
| 7,796,243 B2 | 9/2010 | Choo-Smith et al. |
| 7,806,687 B2 | 10/2010 | Minagi et al. |
| 7,806,727 B2 | 10/2010 | Dold et al. |
| 7,813,787 B2 | 10/2010 | de Josselin de Jong et al. |
| 7,824,180 B2 | 11/2010 | Abolfathi et al. |
| 7,841,464 B2 | 11/2010 | Cinader et al. |
| 7,845,969 B2 | 12/2010 | Stadler et al. |
| 7,854,609 B2 | 12/2010 | Chen et al. |
| 7,862,336 B2 | 1/2011 | Kopelman et al. |
| 7,869,983 B2 | 1/2011 | Raby et al. |
| 7,872,760 B2 | 1/2011 | Ertl |
| 7,874,836 B2 | 1/2011 | McSurdy |
| 7,874,837 B2 | 1/2011 | Chishti et al. |
| 7,874,849 B2 | 1/2011 | Sticker et al. |
| 7,878,801 B2 | 2/2011 | Abolfathi et al. |
| 7,878,805 B2 | 2/2011 | Moss et al. |
| 7,880,751 B2 | 2/2011 | Kuo et al. |
| 7,892,474 B2 | 2/2011 | Shkolnik et al. |
| 7,904,308 B2 | 3/2011 | Arnone et al. |
| 7,907,280 B2 | 3/2011 | Johs et al. |
| 7,929,151 B2 | 4/2011 | Liang et al. |
| 7,930,189 B2 | 4/2011 | Kuo |
| 7,947,508 B2 | 5/2011 | Tricca et al. |
| 7,959,308 B2 | 6/2011 | Freeman et al. |
| 7,963,766 B2 | 6/2011 | Cronauer |
| 7,970,627 B2 | 6/2011 | Kuo et al. |
| 7,985,414 B2 | 7/2011 | Knaack et al. |
| 7,986,415 B2 | 7/2011 | Thiel et al. |
| 7,987,099 B2 | 7/2011 | Kuo et al. |
| 7,991,485 B2 | 8/2011 | Zakim |
| 8,017,891 B2 | 9/2011 | Nevin |
| 8,026,916 B2 | 9/2011 | Wen |
| 8,027,709 B2 | 9/2011 | Arnone et al. |
| 8,029,277 B2 | 10/2011 | Imgrund et al. |
| 8,038,444 B2 | 10/2011 | Kitching et al. |
| 8,045,772 B2 | 10/2011 | Kosuge et al. |
| 8,075,306 B2 | 12/2011 | Kitching et al. |
| 8,077,949 B2 | 12/2011 | Liang et al. |
| 8,092,215 B2 | 1/2012 | Stone-Collonge et al. |
| 8,095,383 B2 | 1/2012 | Arnone et al. |
| 8,099,268 B2 | 1/2012 | Kitching et al. |
| 8,099,305 B2 | 1/2012 | Kuo et al. |
| 8,108,189 B2 | 1/2012 | Chelnokov et al. |
| 8,118,592 B2 | 2/2012 | Tortorici |
| 8,126,025 B2 | 2/2012 | Takeda |
| 8,136,529 B2 | 3/2012 | Kelly |
| 8,144,954 B2 | 3/2012 | Quadling et al. |
| 8,152,518 B2 | 4/2012 | Kuo |
| 8,160,334 B2 | 4/2012 | Thiel et al. |
| 8,172,569 B2 | 5/2012 | Matty et al. |
| 8,197,252 B1 | 6/2012 | Harrison |
| 8,201,560 B2 | 6/2012 | Dembro |
| 8,240,018 B2 | 8/2012 | Walter et al. |
| 8,275,180 B2 | 9/2012 | Kuo |
| 8,292,617 B2 | 10/2012 | Brandt et al. |
| 8,294,657 B2 | 10/2012 | Kim et al. |
| 8,296,952 B2 | 10/2012 | Greenberg |
| 8,306,608 B2 | 11/2012 | Mandelis et al. |
| 8,314,764 B2 | 11/2012 | Kim et al. |
| 8,332,015 B2 | 12/2012 | Ertl |
| 8,401,826 B2 | 3/2013 | Cheng et al. |
| 8,433,083 B2 | 4/2013 | Abolfathi et al. |
| 8,439,672 B2 | 5/2013 | Matov et al. |
| 8,465,280 B2 | 6/2013 | Sachdeva et al. |
| 8,488,113 B2 | 7/2013 | Thiel et al. |
| 8,523,565 B2 | 9/2013 | Matty et al. |
| 8,545,221 B2 | 10/2013 | Stone-Collonge et al. |
| 8,556,625 B2 | 10/2013 | Lovely |
| 8,639,477 B2 | 1/2014 | Chelnokov et al. |
| 8,650,586 B2 | 2/2014 | Lee et al. |
| 8,738,394 B2 | 5/2014 | Kuo |
| 8,771,149 B2 | 7/2014 | Rahman et al. |
| 8,843,381 B2 | 9/2014 | Kuo et al. |
| 8,870,566 B2 | 10/2014 | Bergersen |
| 8,874,452 B2 | 10/2014 | Kuo |
| 8,899,976 B2 | 12/2014 | Chen et al. |
| 8,944,812 B2 | 2/2015 | Kou |
| 8,992,216 B2 | 3/2015 | Karazivan |
| 9,004,915 B2 | 4/2015 | Moss et al. |
| 9,039,418 B1 | 5/2015 | Rubbed |
| 9,084,535 B2 | 7/2015 | Girkin et al. |
| 9,084,657 B2 | 7/2015 | Matty et al. |
| 9,211,166 B2 | 12/2015 | Kuo et al. |
| 9,214,014 B2 | 12/2015 | Levin |
| 9,220,580 B2 | 12/2015 | Borovinskih et al. |
| 9,241,774 B2 | 1/2016 | Li et al. |
| 9,277,972 B2 | 3/2016 | Brandt et al. |
| 9,403,238 B2 | 8/2016 | Culp |
| 9,414,897 B2 | 8/2016 | Wu et al. |
| 9,463,287 B1 | 10/2016 | Lorberbaum et al. |
| 9,492,243 B2 | 11/2016 | Kuo |
| 9,566,132 B2 | 2/2017 | Stone-Collonge et al. |
| 9,589,329 B2 | 3/2017 | Levin |
| 9,675,427 B2 | 6/2017 | Kopelman |

(56) References Cited

U.S. PATENT DOCUMENTS

| | | |
|---|---|---|
| 9,730,769 B2 | 8/2017 | Chen et al. |
| 9,820,829 B2 | 11/2017 | Kuo |
| 9,830,688 B2 | 11/2017 | Levin |
| 9,844,421 B2 | 12/2017 | Moss et al. |
| 9,848,985 B2 | 12/2017 | Yang et al. |
| 10,123,706 B2 | 11/2018 | Elbaz et al. |
| 10,123,853 B2 | 11/2018 | Moss et al. |
| 10,154,889 B2 | 12/2018 | Chen et al. |
| 10,172,693 B2 | 1/2019 | Brandt et al. |
| 10,195,690 B2 | 2/2019 | Culp |
| 10,231,801 B2 | 3/2019 | Korytov et al. |
| 10,238,472 B2 | 3/2019 | Levin |
| 10,248,883 B2 | 4/2019 | Borovinskih et al. |
| 10,258,432 B2 | 4/2019 | Webber |
| 10,275,862 B2 | 4/2019 | Levin |
| 2001/0002310 A1 | 5/2001 | Chishti et al. |
| 2001/0032100 A1 | 10/2001 | Mahmud et al. |
| 2001/0038705 A1 | 11/2001 | Rubbert et al. |
| 2001/0041320 A1 | 11/2001 | Phan et al. |
| 2002/0004727 A1 | 1/2002 | Knaus et al. |
| 2002/0007284 A1 | 1/2002 | Schurenberg et al. |
| 2002/0010568 A1 | 1/2002 | Rubbert et al. |
| 2002/0015934 A1 | 2/2002 | Rubbert et al. |
| 2002/0025503 A1 | 2/2002 | Chapoulaud et al. |
| 2002/0026105 A1 | 2/2002 | Drazen |
| 2002/0028417 A1 | 3/2002 | Chapoulaud et al. |
| 2002/0035572 A1 | 3/2002 | Takatori et al. |
| 2002/0064752 A1 | 5/2002 | Durbin et al. |
| 2002/0064759 A1 | 5/2002 | Durbin et al. |
| 2002/0087551 A1 | 7/2002 | Hickey et al. |
| 2002/0107853 A1 | 8/2002 | Hofmann et al. |
| 2002/0188478 A1 | 12/2002 | Breeland et al. |
| 2002/0192617 A1 | 12/2002 | Phan et al. |
| 2003/0000927 A1 | 1/2003 | Kanaya et al. |
| 2003/0008259 A1 | 1/2003 | Kuo et al. |
| 2003/0009252 A1 | 1/2003 | Pavlovskaia et al. |
| 2003/0019848 A1 | 1/2003 | Nicholas et al. |
| 2003/0021453 A1 | 1/2003 | Weise et al. |
| 2003/0035061 A1 | 2/2003 | Iwaki et al. |
| 2003/0049581 A1 | 3/2003 | Deluke |
| 2003/0057192 A1 | 3/2003 | Patel |
| 2003/0059736 A1 | 3/2003 | Lai et al. |
| 2003/0060532 A1 | 3/2003 | Subelka et al. |
| 2003/0068598 A1 | 4/2003 | Vallittu et al. |
| 2003/0095697 A1 | 5/2003 | Wood et al. |
| 2003/0101079 A1 | 5/2003 | McLaughlin |
| 2003/0103060 A1 | 6/2003 | Anderson et al. |
| 2003/0120517 A1 | 6/2003 | Eida et al. |
| 2003/0139834 A1 | 7/2003 | Nikolskiy et al. |
| 2003/0144886 A1 | 7/2003 | Taira |
| 2003/0172043 A1 | 9/2003 | Guyon et al. |
| 2003/0192867 A1 | 10/2003 | Yamazaki et al. |
| 2003/0207224 A1 | 11/2003 | Lotte |
| 2003/0211440 A1 | 11/2003 | Kuo et al. |
| 2003/0215764 A1 | 11/2003 | Kopelman et al. |
| 2003/0224311 A1 | 12/2003 | Cronauer |
| 2003/0224313 A1 | 12/2003 | Bergersen |
| 2003/0224314 A1 | 12/2003 | Bergersen |
| 2004/0002873 A1 | 1/2004 | Sachdeva |
| 2004/0009449 A1 | 1/2004 | Mah et al. |
| 2004/0013994 A1 | 1/2004 | Goldberg et al. |
| 2004/0019262 A1 | 1/2004 | Perelgut |
| 2004/0029078 A1 | 2/2004 | Marshall |
| 2004/0038168 A1 | 2/2004 | Choi et al. |
| 2004/0054304 A1 | 3/2004 | Raby |
| 2004/0054358 A1 | 3/2004 | Cox et al. |
| 2004/0058295 A1 | 3/2004 | Bergersen |
| 2004/0068199 A1 | 4/2004 | Echauz et al. |
| 2004/0078222 A1 | 4/2004 | Khan et al. |
| 2004/0080621 A1 | 4/2004 | Fisher et al. |
| 2004/0094165 A1 | 5/2004 | Cook |
| 2004/0107118 A1 | 6/2004 | Harnsberger et al. |
| 2004/0133083 A1 | 7/2004 | Comaniciu et al. |
| 2004/0152036 A1 | 8/2004 | Abolfathi |
| 2004/0158194 A1 | 8/2004 | Wolff et al. |
| 2004/0166463 A1 | 8/2004 | Wen et al. |
| 2004/0167646 A1 | 8/2004 | Jelonek et al. |
| 2004/0170941 A1* | 9/2004 | Phan .................. A61C 7/00 433/6 |
| 2004/0193036 A1 | 9/2004 | Zhou et al. |
| 2004/0197728 A1 | 10/2004 | Abolfathi et al. |
| 2004/0214128 A1 | 10/2004 | Sachdeva et al. |
| 2004/0219479 A1* | 11/2004 | Malin .................. A61C 1/084 433/75 |
| 2004/0220691 A1 | 11/2004 | Hofmeister et al. |
| 2004/0229185 A1 | 11/2004 | Knopp |
| 2004/0259049 A1 | 12/2004 | Kopelman et al. |
| 2005/0003318 A1 | 1/2005 | Choi et al. |
| 2005/0023356 A1 | 2/2005 | Wiklof et al. |
| 2005/0031196 A1 | 2/2005 | Moghaddam et al. |
| 2005/0037312 A1 | 2/2005 | Uchida |
| 2005/0037320 A1* | 2/2005 | Poirier .................. A61C 1/084 433/173 |
| 2005/0038669 A1 | 2/2005 | Sachdeva et al. |
| 2005/0040551 A1 | 2/2005 | Biegler et al. |
| 2005/0042569 A1 | 2/2005 | Plan et al. |
| 2005/0042577 A1 | 2/2005 | Kvitrud et al. |
| 2005/0048433 A1 | 3/2005 | Hilliard |
| 2005/0074717 A1 | 4/2005 | Cleary et al. |
| 2005/0089822 A1 | 4/2005 | Geng |
| 2005/0100333 A1 | 5/2005 | Kerschbaumer et al. |
| 2005/0108052 A1 | 5/2005 | Omaboe |
| 2005/0131738 A1 | 6/2005 | Morris |
| 2005/0144150 A1 | 6/2005 | Ramamurthy et al. |
| 2005/0171594 A1 | 8/2005 | Machan et al. |
| 2005/0171630 A1 | 8/2005 | Dinauer et al. |
| 2005/0181333 A1 | 8/2005 | Karazivan et al. |
| 2005/0186524 A1 | 8/2005 | Abolfathi et al. |
| 2005/0186526 A1 | 8/2005 | Stewart et al. |
| 2005/0216314 A1 | 9/2005 | Secor |
| 2005/0233276 A1 | 10/2005 | Kopelman et al. |
| 2005/0239013 A1 | 10/2005 | Sachdeva |
| 2005/0244781 A1 | 11/2005 | Abels et al. |
| 2005/0244791 A1 | 11/2005 | Davis et al. |
| 2005/0271996 A1 | 12/2005 | Sporbert et al. |
| 2006/0008760 A1 | 1/2006 | Phan et al. |
| 2006/0056670 A1 | 3/2006 | Hamadeh |
| 2006/0057533 A1 | 3/2006 | McGann |
| 2006/0063135 A1 | 3/2006 | Mehl |
| 2006/0078842 A1 | 4/2006 | Sachdeva et al. |
| 2006/0084024 A1 | 4/2006 | Farrell |
| 2006/0093982 A1 | 5/2006 | Wen |
| 2006/0098007 A1 | 5/2006 | Rouet et al. |
| 2006/0099545 A1 | 5/2006 | Lia et al. |
| 2006/0099546 A1 | 5/2006 | Bergersen |
| 2006/0110698 A1 | 5/2006 | Robson |
| 2006/0111631 A1 | 5/2006 | Kelliher et al. |
| 2006/0115782 A1 | 6/2006 | Li et al. |
| 2006/0115785 A1 | 6/2006 | Li et al. |
| 2006/0137813 A1 | 6/2006 | Robrecht et al. |
| 2006/0147872 A1 | 7/2006 | Andreiko |
| 2006/0154198 A1 | 7/2006 | Durbin et al. |
| 2006/0154207 A1 | 7/2006 | Kuo |
| 2006/0173715 A1 | 8/2006 | Wang |
| 2006/0183082 A1 | 8/2006 | Quadling et al. |
| 2006/0188834 A1 | 8/2006 | Hilliard |
| 2006/0188848 A1 | 8/2006 | Tricca et al. |
| 2006/0194163 A1* | 8/2006 | Tricca .................. A61C 7/00 433/24 |
| 2006/0199153 A1 | 9/2006 | Liu et al. |
| 2006/0204078 A1 | 9/2006 | Orth et al. |
| 2006/0223022 A1 | 10/2006 | Solomon |
| 2006/0223023 A1 | 10/2006 | Lai et al. |
| 2006/0223032 A1 | 10/2006 | Fried et al. |
| 2006/0223342 A1 | 10/2006 | Borst et al. |
| 2006/0234179 A1 | 10/2006 | Wen et al. |
| 2006/0257815 A1 | 11/2006 | De Dominicis |
| 2006/0275729 A1 | 12/2006 | Fornoff |
| 2006/0275731 A1 | 12/2006 | Huafeng et al. |
| 2006/0275736 A1 | 12/2006 | Wen et al. |
| 2006/0277075 A1 | 12/2006 | Salwan |
| 2006/0290693 A1 | 12/2006 | Zhou et al. |
| 2006/0292520 A1 | 12/2006 | Dillon et al. |
| 2007/0031775 A1 | 2/2007 | Andreiko |

(56) References Cited

U.S. PATENT DOCUMENTS

| | | |
|---|---|---|
| 2007/0046865 A1 | 3/2007 | Umeda et al. |
| 2007/0053048 A1 | 3/2007 | Kumar et al. |
| 2007/0054237 A1 | 3/2007 | Neuschafer |
| 2007/0065768 A1 | 3/2007 | Nadav |
| 2007/0087300 A1 | 4/2007 | Willison et al. |
| 2007/0087302 A1 | 4/2007 | Reising et al. |
| 2007/0106138 A1 | 5/2007 | Beiski et al. |
| 2007/0122592 A1 | 5/2007 | Anderson et al. |
| 2007/0128574 A1 | 6/2007 | Kuo et al. |
| 2007/0141525 A1 | 6/2007 | Cinader, Jr. |
| 2007/0141526 A1 | 6/2007 | Eisenberg et al. |
| 2007/0143135 A1 | 6/2007 | Lindquist et al. |
| 2007/0168152 A1 | 7/2007 | Matov et al. |
| 2007/0172112 A1 | 7/2007 | Paley et al. |
| 2007/0172291 A1 | 7/2007 | Yokoyama |
| 2007/0178420 A1 | 8/2007 | Keski-Nisula et al. |
| 2007/0183633 A1 | 8/2007 | Hoffmann |
| 2007/0184402 A1 | 8/2007 | Boutoussov et al. |
| 2007/0185732 A1 | 8/2007 | Hicks et al. |
| 2007/0192137 A1 | 8/2007 | Ombrellaro |
| 2007/0199929 A1 | 8/2007 | Rippl et al. |
| 2007/0207434 A1 | 9/2007 | Kuo et al. |
| 2007/0215582 A1 | 9/2007 | Roeper et al. |
| 2007/0218422 A1 | 9/2007 | Ehrenfeld |
| 2007/0231765 A1 | 10/2007 | Phan et al. |
| 2007/0238065 A1 | 10/2007 | Sherwood et al. |
| 2007/0239488 A1 | 10/2007 | DeRosso |
| 2007/0263226 A1 | 11/2007 | Kurtz et al. |
| 2008/0013727 A1 | 1/2008 | Uemura |
| 2008/0020350 A1 | 1/2008 | Matov et al. |
| 2008/0045053 A1 | 2/2008 | Stadler et al. |
| 2008/0057461 A1 | 3/2008 | Cheng et al. |
| 2008/0057467 A1* | 3/2008 | Gittelson ............... A61C 1/084 433/72 |
| 2008/0057479 A1 | 3/2008 | Grenness |
| 2008/0059238 A1 | 3/2008 | Park et al. |
| 2008/0090208 A1 | 4/2008 | Rubbert |
| 2008/0094389 A1 | 4/2008 | Rouet et al. |
| 2008/0113317 A1 | 5/2008 | Kemp et al. |
| 2008/0115791 A1 | 5/2008 | Heine |
| 2008/0118882 A1 | 5/2008 | Su |
| 2008/0118886 A1 | 5/2008 | Liang et al. |
| 2008/0141534 A1 | 6/2008 | Hilliard |
| 2008/0169122 A1 | 7/2008 | Shiraishi et al. |
| 2008/0171934 A1 | 7/2008 | Greenan et al. |
| 2008/0176448 A1 | 7/2008 | Muller et al. |
| 2008/0233530 A1 | 9/2008 | Cinader |
| 2008/0242144 A1 | 10/2008 | Dietz |
| 2008/0248443 A1 | 10/2008 | Chishti et al. |
| 2008/0254403 A1 | 10/2008 | Hilliard |
| 2008/0268400 A1 | 10/2008 | Moss et al. |
| 2008/0306724 A1 | 12/2008 | Kitching et al. |
| 2009/0029310 A1 | 1/2009 | Pumphrey et al. |
| 2009/0030290 A1 | 1/2009 | Kozuch et al. |
| 2009/0030347 A1 | 1/2009 | Cao |
| 2009/0040740 A1 | 2/2009 | Muller et al. |
| 2009/0061379 A1 | 3/2009 | Yamamoto et al. |
| 2009/0061381 A1 | 3/2009 | Durbin et al. |
| 2009/0075228 A1 | 3/2009 | Kumada et al. |
| 2009/0087050 A1 | 4/2009 | Gandyra |
| 2009/0098502 A1 | 4/2009 | Andreiko |
| 2009/0099445 A1* | 4/2009 | Burger .................. A61B 90/36 600/424 |
| 2009/0103579 A1 | 4/2009 | Ushimaru et al. |
| 2009/0105523 A1 | 4/2009 | Kassayan et al. |
| 2009/0130620 A1 | 5/2009 | Yazdi et al. |
| 2009/0136890 A1 | 5/2009 | Kang et al. |
| 2009/0136893 A1 | 5/2009 | Zegarelli |
| 2009/0148809 A1 | 6/2009 | Kuo et al. |
| 2009/0170050 A1 | 7/2009 | Marcus |
| 2009/0181346 A1 | 7/2009 | Orth |
| 2009/0191502 A1 | 7/2009 | Cao et al. |
| 2009/0210032 A1 | 8/2009 | Beiski et al. |
| 2009/0218514 A1 | 9/2009 | Klunder et al. |
| 2009/0281433 A1 | 11/2009 | Saadat et al. |
| 2009/0286195 A1 | 11/2009 | Sears et al. |
| 2009/0298017 A1 | 12/2009 | Boerjes et al. |
| 2009/0316966 A1 | 12/2009 | Marshall et al. |
| 2010/0019170 A1 | 1/2010 | Hart et al. |
| 2010/0028825 A1 | 2/2010 | Lemchen |
| 2010/0045902 A1 | 2/2010 | Ikeda et al. |
| 2010/0062394 A1 | 3/2010 | Jones et al. |
| 2010/0068676 A1 | 3/2010 | Mason et al. |
| 2010/0145664 A1 | 6/2010 | Hultgren et al. |
| 2010/0145898 A1 | 6/2010 | Malfliet et al. |
| 2010/0165275 A1 | 7/2010 | Tsukamoto et al. |
| 2010/0179789 A1 | 7/2010 | Sachdeva et al. |
| 2010/0196837 A1 | 8/2010 | Farrell |
| 2010/0217130 A1 | 8/2010 | Weinlaender |
| 2010/0231577 A1 | 9/2010 | Kim et al. |
| 2010/0268363 A1 | 10/2010 | Karim et al. |
| 2010/0279243 A1 | 11/2010 | Cinader et al. |
| 2010/0280798 A1 | 11/2010 | Pattijn |
| 2010/0281370 A1 | 11/2010 | Rohaly et al. |
| 2011/0102549 A1 | 5/2011 | Takahashi |
| 2011/0102566 A1 | 5/2011 | Zakian et al. |
| 2011/0104630 A1 | 5/2011 | Matov et al. |
| 2011/0164810 A1 | 7/2011 | Zang et al. |
| 2012/0166213 A1 | 6/2012 | Arnone et al. |
| 2013/0103176 A1 | 4/2013 | Kopelman et al. |
| 2014/0081091 A1 | 3/2014 | Abolfathi et al. |
| 2014/0136222 A1 | 5/2014 | Arnone et al. |
| 2014/0142902 A1 | 5/2014 | Chelnokov et al. |
| 2014/0280376 A1 | 9/2014 | Kuo |
| 2015/0004553 A1 | 1/2015 | Li et al. |
| 2015/0132708 A1 | 5/2015 | Kuo |
| 2015/0173856 A1 | 6/2015 | Iowe et al. |
| 2015/0238283 A1 | 8/2015 | Tanugula et al. |
| 2015/0320320 A1 | 11/2015 | Kopelman et al. |
| 2015/0320532 A1 | 11/2015 | Matty et al. |
| 2016/0003610 A1 | 1/2016 | Lampert et al. |
| 2016/0051345 A1 | 2/2016 | Levin |
| 2016/0064898 A1 | 3/2016 | Atiya et al. |
| 2016/0081768 A1 | 3/2016 | Kopelman et al. |
| 2016/0081769 A1 | 3/2016 | Kimura et al. |
| 2016/0095668 A1 | 4/2016 | Kuo et al. |
| 2016/0106520 A1 | 4/2016 | Borovinskih et al. |
| 2016/0120621 A1 | 5/2016 | Li et al. |
| 2016/0135924 A1 | 5/2016 | Choi et al. |
| 2016/0135925 A1 | 5/2016 | Mason et al. |
| 2016/0163115 A1 | 6/2016 | Furst |
| 2016/0217708 A1 | 7/2016 | Levin et al. |
| 2016/0302885 A1 | 10/2016 | Matov et al. |
| 2016/0338799 A1 | 11/2016 | Wu et al. |
| 2016/0367339 A1 | 12/2016 | Khardekar et al. |
| 2017/0007366 A1 | 1/2017 | Kopelman et al. |
| 2017/0007367 A1 | 1/2017 | Li et al. |
| 2017/0007368 A1 | 1/2017 | Boronkay |
| 2017/0020633 A1 | 1/2017 | Stone-Collonge et al. |
| 2017/0100212 A1 | 4/2017 | Sherwood et al. |
| 2017/0100213 A1 | 4/2017 | Kuo |
| 2017/0105815 A1 | 4/2017 | Matov et al. |
| 2017/0135792 A1 | 5/2017 | Webber |
| 2017/0135793 A1 | 5/2017 | Webber et al. |
| 2017/0156821 A1 | 6/2017 | Kopelman et al. |
| 2017/0165032 A1 | 6/2017 | Webber et al. |
| 2017/0258555 A1 | 9/2017 | Kopelman |
| 2017/0319296 A1 | 11/2017 | Webber et al. |
| 2018/0000563 A1 | 1/2018 | Shanjani et al. |
| 2018/0000565 A1 | 1/2018 | Shanjani et al. |
| 2018/0028064 A1 | 2/2018 | Elbaz et al. |
| 2018/0028065 A1 | 2/2018 | Elbaz et al. |
| 2018/0055602 A1 | 3/2018 | Kopelman et al. |
| 2018/0071055 A1 | 3/2018 | Kuo |
| 2018/0125610 A1 | 5/2018 | Carrier et al. |
| 2018/0153648 A1 | 6/2018 | Shanjani et al. |
| 2018/0153649 A1 | 6/2018 | Wu et al. |
| 2018/0153733 A1 | 6/2018 | Kuo |
| 2018/0168788 A1 | 6/2018 | Fernie |
| 2018/0192877 A1 | 7/2018 | Atiya et al. |
| 2018/0228359 A1 | 8/2018 | Meyer et al. |
| 2018/0280118 A1 | 10/2018 | Cramer |
| 2018/0284727 A1 | 10/2018 | Cramer et al. |
| 2018/0318043 A1 | 11/2018 | Li et al. |

(56) References Cited

U.S. PATENT DOCUMENTS

| | | |
|---|---|---|
| 2018/0353264 A1 | 12/2018 | Riley et al. |
| 2018/0360567 A1 | 12/2018 | Xue et al. |
| 2018/0368944 A1 | 12/2018 | Sato et al. |
| 2018/0368961 A1 | 12/2018 | Shanjani et al. |
| 2019/0019187 A1 | 1/2019 | Miller et al. |
| 2019/0021817 A1 | 1/2019 | Sato et al. |
| 2019/0029522 A1 | 1/2019 | Sato et al. |
| 2019/0029784 A1 | 1/2019 | Moalem et al. |
| 2019/0046296 A1 | 2/2019 | Kopelman et al. |
| 2019/0046297 A1 | 2/2019 | Kopelman et al. |
| 2019/0069975 A1 | 3/2019 | Cam et al. |
| 2019/0076026 A1 | 3/2019 | Elbaz et al. |
| 2019/0076214 A1 | 3/2019 | Nyukhtikov et al. |
| 2019/0076216 A1 | 3/2019 | Moss et al. |
| 2019/0090983 A1 | 3/2019 | Webber et al. |
| 2019/0095539 A1 | 3/2019 | Elbaz et al. |
| 2019/0099129 A1 | 4/2019 | Kopelman et al. |
| 2019/0105130 A1 | 4/2019 | Grove et al. |
| 2019/0183614 A1 | 6/2019 | Levin |

FOREIGN PATENT DOCUMENTS

| | | |
|---|---|---|
| CA | 1121955 A1 | 4/1982 |
| CN | 1655732 A | 8/2005 |
| CN | 1655733 A | 8/2005 |
| CN | 1867317 A | 11/2006 |
| CN | 102017658 A | 4/2011 |
| DE | 2749802 A1 | 5/1978 |
| DE | 3526198 A1 | 2/1986 |
| DE | 4207169 A1 | 9/1993 |
| DE | 69327661 T2 | 7/2000 |
| DE | 102005043627 A1 | 3/2007 |
| EP | 0428152 A1 | 5/1991 |
| EP | 490848 A2 | 6/1992 |
| EP | 541500 A1 | 5/1993 |
| EP | 714632 B1 | 5/1997 |
| EP | 774933 B1 | 12/2000 |
| EP | 731673 B1 | 5/2001 |
| EP | 1941843 A2 | 7/2008 |
| EP | 1989764 B1 | 7/2012 |
| ES | 463897 A1 | 1/1980 |
| FR | 2369828 A1 | 6/1978 |
| FR | 2867377 A1 | 9/2005 |
| FR | 2930334 A1 | 10/2009 |
| GB | 1550777 A | 8/1979 |
| JP | 53-058191 A | 5/1978 |
| JP | 04-028359 A | 1/1992 |
| JP | 08-508174 A | 9/1996 |
| JP | 09-19443 A | 1/1997 |
| JP | 2003245289 A | 9/2003 |
| JP | 2004515261 A | 5/2004 |
| JP | 2000339468 A | 9/2004 |
| JP | 2005527320 A | 9/2005 |
| JP | 2005527321 A | 9/2005 |
| JP | 2006043121 A | 2/2006 |
| JP | 2006511243 | 4/2006 |
| JP | 2007151614 A | 6/2007 |
| JP | 2007260158 A | 10/2007 |
| JP | 2007537824 A | 12/2007 |
| JP | 2008067732 A | 3/2008 |
| JP | 2008523370 A | 7/2008 |
| JP | 04184427 B1 | 11/2008 |
| JP | 2009000412 A | 1/2009 |
| JP | 2009018173 A | 1/2009 |
| JP | 2009078133 A | 4/2009 |
| JP | 2009101386 A | 5/2009 |
| JP | 2009205330 A | 9/2009 |
| KR | 10-20020062793 A | 7/2002 |
| KR | 10-20070108019 A | 11/2007 |
| KR | 10-20090065778 A | 6/2009 |
| TW | 480166 B | 3/2002 |
| WO | WO91/004713 A1 | 4/1991 |
| WO | WO92/03102 A1 | 3/1992 |
| WO | WO94/010935 A1 | 5/1994 |
| WO | WO96/23452 A1 | 8/1996 |
| WO | WO98/032394 A1 | 7/1998 |
| WO | WO98/044865 A1 | 10/1998 |
| WO | WO01/08592 A1 | 2/2001 |
| WO | 0180762 A2 | 11/2001 |
| WO | WO01/85047 A2 | 11/2001 |
| WO | WO02/017776 A2 | 3/2002 |
| WO | WO02/024100 A1 | 3/2002 |
| WO | WO02/058583 A1 | 8/2002 |
| WO | WO02/062252 A1 | 8/2002 |
| WO | WO02/095475 A1 | 11/2002 |
| WO | WO03/003932 A2 | 1/2003 |
| WO | WO2005/114183 A1 | 12/2005 |
| WO | WO2006/096558 A2 | 9/2006 |
| WO | WO2006/100700 A1 | 9/2006 |
| WO | WO2006/133548 A1 | 12/2006 |
| WO | WO2007/019709 A2 | 2/2007 |
| WO | WO2007/071341 A1 | 6/2007 |
| WO | WO2007/103377 A2 | 9/2007 |
| WO | WO2008/115654 A1 | 9/2008 |
| WO | WO2009/016645 A2 | 2/2009 |
| WO | WO2009/085752 A2 | 7/2009 |
| WO | WO2009/089129 A1 | 7/2009 |

OTHER PUBLICATIONS

Sarment et al., "Accuracy of implant placement with a stereolithographic surgical guide," Int J Oral Maxillofac Implants, 2003; 18:571-577.

Di Giacomo et al., "Clinical application of stereolithographic surgical guides for implant placement: Preliminary results," J Periodontol. 2005; 76:503-507.

Rose, et al., "The Role of Orthodontics in Implant Dentistry", British Dental Journal, vol. 201, No. 12, Dec. 23, 2006, pp. 753-764.

Office Action from related Japan Patent Application No. 2015-258364, dated Apr. 25, 2017, 11 pages.

Partial Search Report from related European Patent Application No. 17154934.8, dated May 12, 2017, 13 pages.

Notice of Allowance from related Japan Patent Application No. 2015-248364, dated Aug. 1, 2018, 3 pages.

Denial of Entry of Amendment from related Japan Patent Application No. 2015-248364, dated Jan. 31, 2018, 10 pages.

Notice of Final Rejection from related Japan Patent Application No. 2015-248363, dated Jan. 29, 2018, 3 pages.

Mantzikos, et al., "Case Report: Forced Eruption and Implant Site Development"; The Angle Orthodontist, vol. 68, No. 2 (1998) (8 pgs).

Smalley, "Implants for Tooth Movement: Determining Implant Location and Orientation"; Journal of Esthetic Dentistry, vol. 7, No. 2 (1995) (11 pgs).

AADR. American Association for Dental Research; Summary of Activities; Los Angeles, CA; p. 195; Mar. 20-23,(year of pub. sufficiently earlier than effective US filing date and any foreign priority date) 1980.

Alcaniz et aL; An Advanced System for the Simulation and Planning of Orthodontic Treatments; Karl Heinz Hohne and Ron Kikinis (eds.); Visualization in Biomedical Computing, 4th Intl. Conf, VBC '96, Hamburg, Germany; Springer-Verlag; pp. 511-520; Sep. 22-25, 1996.

Alexander et al.; The DigiGraph Work Station Part 2 Clinical Management; J. Clin. Orthod.; pp. 402-407; (Author Manuscript); Jul. 1990.

Align Technology; Align technology announces new teen solution with introduction of invisalign teen with mandibular advancement; 2 pages; retrieved from the internet (http://investor.aligntech.com/static-files/eb4fa6bb-3e62-404f-b74d-32059366a01b); Mar. 6, 2017.

Allesee Orthodontic Appliance: Important Tip About Wearing the Red White & Blue Active Clear Retainer System; Allesee Orthodontic Appliances—Pro Lab; 1 page; (year of pub. sufficiently earlier than effective US filed and any foreign priority date); 1998.

Allesee Orthodontic Appliances: DuraClearTM; Product information; 1 page; (year of pub. sufficiently earlier than effective US filed and any foreign priority date) 1997.

Allesee Orthodontic Appliances; The Choice Is Clear: Red, White & Blue . . . The Simple, Affordable, No-Braces Treatment; ( product

(56) References Cited

OTHER PUBLICATIONS information for doctors); retrieved from the internet (http://ormco.com/aoa/appliancesservices/RWB/doctorhtml); 5 pages on May 19, 2003.
Allesee Orthodontic Appliances; The Choice Is Clear: Red, White & Blue . . . The Simple, Affordable, No-Braces Treatment; (product information), 6 pages; (year of pub. sufficiently earlier than effective US filed and any foreign priority date) 2003.
Allesee Orthodontic Appliances; The Choice is Clear: Red, White & Blue . . . The Simple, Affordable, No-Braces Treatment;(Patient Information); retrieved from the internet (http://ormco.com/aoa/appliancesservices/RWB/patients.html); 2 pages on May 19, 2003.
Allesee Orthodontic Appliances; The Red, White & Blue Way to Improve Your Smile; (information for patients), 2 pages; (year of pub. sufficiently earlier than effective US filing date and any foreign priority date) 1992.
Allesee Orthodontic Appliances; You may be a candidate for this invisible no-braces treatment; product information for patients; 2 pages; (year of pub. sufficiently earlier than effective US filing date and any foreign priority date) 2002.
Altschuler et al.; Analysis of 3-D Data for Comparative 3-D Serial Growth Pattern Studies of Oral-Facial Structures; AADR Abstracts, Program and Abstracts of Papers, 57th General Session, IADR Annual Session, Mar. 29, 1979-Apr. 1, 1979, New Orleans Marriot; Journal of Dental Research; vol. 58, Special Issue A, p. 221; Jan. 1979.
Altschuler et al.; Laser Electro-Optic System for Rapid Three-Dimensional (3D) Topographic Mapping of Surfaces; Optical Engineering; 20(6); pp. 953-961; Dec. 1981.
Altschuler et al.; Measuring Surfaces Space-Coded by a Laser-Projected Dot Matrix; SPIE Imaging q Applications for Automated Industrial Inspection and Assembly; vol. 182; pp. 187-191; Oct. 10, 1979.
Altschuler; 3D Mapping of Maxillo-Facial Prosthesis; AADR Abstract #607; 2 pages total, (year of pub. sufficiently earlier than effective US filing date and any foreign priority date) 1980.
Andersson et al.; Clinical Results with Titanium Crowns Fabricated with Machine Duplication and Spark Erosion; Acta Odontologica Scandinavica; 47(5); pp. 279-286; Oct. 1989.
Andrews, The Six Keys to Optimal Occlusion Straight Wire, Chapter 3, L.A. Wells; pp. 13-24; (year of pub. sufficiently earlier than effective US filing date and any foreign priority date) 1989.
Bartels et al.; An Introduction to Splines for Use in Computer Graphics and Geometric Modeling; Morgan Kaufmann Publishers; pp. 422-425 Jan. 1, 1987.
Baumrind et al, "Mapping the Skull in 3-D," reprinted from J. Calif. Dent. Assoc, 48(2), 11 pages; (year of pub. sufficiently earlier than effective US filing date and any foreign priority date) Fall Issue 1972.
Baumrind et al.; A Stereophotogrammetric System for the Detection of Prosthesis Loosening in Total Hip Arthroplasty; NATO Symposium on Applications of Human Biostereometrics; SPIE; vol. 166; pp. 112-123; Jul. 9-13, 1978.
Baumrind; A System for Cranio facial Mapping Through the Integration of Data from Stereo X-Ray Films and Stereo Photographs; an invited paper submitted to the 1975 American Society of Photogram Symposium on Close-Range Photogram Systems; University of Illinois; pp. 142-166; Aug. 26-30, 1975.
Baumrind; Integrated Three-Dimensional Craniofacial Mapping: Background, Principles, and Perspectives; Seminars in Orthodontics; 7(4); pp. 223-232; Dec. 2001.
beautyworlds.com; Virtual plastic surgery—beautysurge.com announces launch of cosmetic surgery digital imaging services; 5 pages; retrieved from the internet (http://www.beautyworlds.com/cosmossurgdigitalimagning.htm); Mar. 2004.
Begole et al.; A Computer System for the Analysis of Dental Casts; The Angle Orthodontist; 51(3); pp. 252-258; Jul. 1981.
Berland; The use of smile libraries for cosmetic dentistry; Dental Tribune: Asia pacfic Edition; pp. 16-18; Mar. 29, 2006.

Bernard et al; Computerized Diagnosis in Orthodontics for Epidemiological Studies: A ProgressReport; (Abstract Only), J. Dental Res. Special Issue, vol. 67, p. 169, paper presented at International Association for Dental Research 66th General Session, Montreal Canada; Mar. 9-13, 1988.
Bhatia et al.; A Computer-Aided Design for Orthognathic Surgery; British Journal of Oral and Maxillofacial Surgery; 22(4); pp. 237-253; Aug. 1, 1984.
Biggerstaff et al.; Computerized Analysis of Occlusion in the Postcanine Dentition; American Journal of Orthodontics; 61(3); pp. 245-254; Mar. 1972.
Biggerstaff; Computerized Diagnostic Setups and Simulations; Angle Orthodontist; 40(1); pp. 28-36; Jan. 1970.
Biostar Operation & Training Manual. Great Lakes Orthodontics, Ltd. 199 Fire Tower Drive,Tonawanda, New York. 14150-5890, 20 pages; (year of pub. sufficiently earlier than effective US filing date and any foreign priority date) 1990.
Blu et al.; Linear interpolation revitalized; IEEE Transactions on Image Processing; 13(5); pp. 710-719; May 2004.
Bookstein; Principal warps: Thin-plate splines and decomposition of deformations; IEEE Transactions on pattern analysis and machine intelligence; 11(6); pp. 567-585; Jun. 1989.
Bourke, Coordinate System Transformation; 1 page; retrived from the internet (http://astronomy.swin.edu.au/' pbourke/prolection/coords) on Nov. 5, 2004; Jun. 1996.
Boyd et al.; Three Dimensional Diagnosis and Orthodontic Treatment of Complex Malocclusions With the Invisalipn Appliance; Seminars in Orthodontics; 7(4); pp. 274-293; Dec. 2001.
Brandestini et al.; Computer Machined Ceramic Inlays: In Vitro Marginal Adaptation; J. Dent. Res. Special Issue; (Abstract 305); vol. 64; p. 208; (year of pub. sufficiently earlier than effective US filing date and any foreign priority date) 1985.
Brook et al.; An Image Analysis System for the Determination of Tooth Dimensions from Study Casts: Comparison with Manual Measurements of Mesio-distal Diameter; Journal of Dental Research; 65(3); pp. 428-431; Mar. 1986.
Burstone et al.; Precision Adjustment of the Transpalatal Lingual Arch: Computer Arch Form Predetermination; American Journal of Orthodontics; 79(2);pp. 115-133; Feb. 1981.
Burstone; Dr. Charles J. Burstone on the Uses of the Computer in Orthodontic Practice (Part 1); Journal of Clinical Orthodontics; 13(7); pp. 442-453; (interview); Jul. 1979.
Burstone; Dr. Charles J. Burstone on the Uses of the Computer in Orthodontic Practice (Part 2); journal of Clinical Orthodontics; 13(8); pp. 539-551 (interview); Aug. 1979.
Cadent Inc.; OrthoCAD ABO user guide; 38 pages; Dec. 21, 2005.
Cadent Inc.; Reviewing and modifying an orthoCAD case; 4 pages; Feb. 14, 2005.
Cardinal Industrial Finishes; Powder Coatings; 6 pages; retrieved from the internet (http://www.cardinalpaint.com) on Aug. 25, 2000.
Carnaghan, An Alternative to Holograms for the Portrayal of Human Teeth; 4th Int'l. Conf. on Holographic Systems, Components and Applications; pp. 228-231; Sep. 15, 1993.
Chaconas et al,; The DigiGraph Work Station, Part 1, Basic Concepts; Journal of Clinical Orthodontics; 24(6); pp. 360-367; (Author Manuscript); Jun. 1990.
Chafetz et al.; Subsidence of the Femoral Prosthesis, A Stereophotogrammetric Evaluation; Clinical Orthopaedics and Related Research; No. 201; pp. 60-67; Dec. 1985.
Chiappone; Constructing the Gnathologic Setup and Positioner; Journal of Clinical Orthodontics; 14(2); pp. 121-133; Feb. 1980.
Chishti et al.; U.S. Appl. No. 60/050,342 entitled "Procedure for moving teeth using a seires of retainers," filed Jun. 20, 1997.
Cottingham; Gnathologic Clear Plastic Positioner; American Journal of Orthodontics; 55(1); pp. 23-31; Jan. 1969.
Crawford; CAD/CAM in the Dental Office: Does It Work?; Canadian Dental Journal; 57(2); pp. 121-123 Feb. 1991.
Crawford; Computers in Dentistry: Part 1: CAD/CAM: The Computer Moves Chairside, Part 2: F. Duret A Man With a Vision, Part 3: The Computer Gives New Vision—Literally, Part 4: Bytes 'N Bites the Computer Moves From the Front Desk to the Operatory; Canadian Dental Journal; 54(9); pp. 661-666 Sep. 1988.

(56) References Cited

OTHER PUBLICATIONS

Crooks; CAD/CAM Comes to USC; USC Dentistry; pp. 14-17; (year of pub. sufficiently earlier than effective US filing date and any foreign priority date) Spring 1990.
CSI Computerized Scanning and Imaging Facility; What is a maximum/minimum intensity projection (MIP/MinIP); 1 page; retrived from the Internet (http://csi.whoi.edu/content/what-maximumminimum-intensity-projection-mipminip); Jan. 4, 2010.
Cureton; Correcting Malaligned Mandibular Incisors with Removable Retainers; Journal of Clinical Orthodontics; 30(7); pp. 390-395; Jul. 1996.
Curry et al.; Integrated Three-Dimensional Craniofacial Mapping at the Craniofacial Research InstrumentationLaboratory/University of the Pacific; Seminars in Orthodontics; 7(4); pp. 258-265; Dec. 2001.
Cutting et al.; Three-Dimensional Computer-Assisted Design of Craniofacial Surgical Procedures: Optimization and Interaction with Cephalometric and CT-Based Models; Plastic and Reconstructive Surgery; 77(6); pp. 877-885; Jun. 1986.
Daniels et al.; The development of the index of complexity outcome and need (ICON); British Journal of Orthodontics; 27(2); pp. 149-162; Jun. 2000.
DCS Dental AG; The CAD/CAM 'DCS Titan System' for Production of Crowns/Bridges; DSC Production; pp. 1-7; Jan. 1992.
Defranco et al.; Three-Dimensional Large Displacement Analysis of Orthodontic Appliances; Journal of Biomechanics; 9(12); pp. 793-801; Jan. 1976.
Dental Institute University of Zurich Switzerland; Program for International Symposium on Computer Restorations: State of the Art of the CEREC-Method; 2 pages; May 1991.
Dentrac Corporation; Dentrac document; pp. 4-13; (year of pub. sufficiently earlier than effective US filing date and any foreign priority date) 1992.
Dentrix; Dentrix G3, new features; 2 pages; retrieved from the internet (http://www.dentrix.com/g3/new_features/index.asp); on Jun. 6, 2008.
Dent-X; Dentsim . . . Dent-x's virtual reality 3-D training simulator . . . A revolution in dental education; 6 pages; retrieved from the internet (http://www.dent-x.com/DentSim.htm); on Sep. 24, 1998.
Di Muzio et al.; Minimum intensity projection (MinIP); 6 pages; retrieved from the internet (https://radiopaedia.org/articles/minimum-intensity-projection-minip) on Sep. 6, 2018.
Doruk et al.; The role of the headgear timer in extraoral co-operation; European Journal of Orthodontics; 26; pp. 289-291; Jun. 1, 2004.
Doyle; Digital Dentistry; Computer Graphics World; pp. 50-52 andp. 54; Oct. 2000.
Duret et al.; CAD/CAM Imaging in Dentistry; Current Opinion in Dentistry; 1 (2); pp. 150-154; Apr. 1991.
Duret et al; CAD-CAM in Dentistry; Journal of the American Dental Association; 117(6); pp. 715-720; Nov. 1988.
Duret; The Dental CAD/CAM, General Description of the Project; Hennson International Product Brochure, 18 pages; Jan. 1986.
Duret; Vers Une Prosthese Informatisee; Tonus; 75(15); pp. 55-57; (English translation attached); 23 pages; Nov. 15, 1985.
Economides; The Microcomputer in the Orthodontic Office; Journal of Clinical Orthodontics; 13(11); pp. 767-772; Nov. 1979.
Elsasser; Some Observations on the History and Uses of the Kesling Positioner; American Journal of Orthodontics; 36(5); pp. 368-374; May 1, 1950.
English translation of Japanese Laid-Open Publication No. 63-11148 to inventor T. Ozukuri (Laid-Open on Jan. 18, 1998) pp. 1-7.
Faber et al.; Computerized Interactive Orthodontic Treatment Planning; American Journal of Orthodontics; 73(1); pp. 36-46; Jan. 1978.
Felton et al.; A Computerized Analysis of the Shape and Stability of Mandibular Arch Form; American Journal of Orthodontics and Dentofacial Orthopedics; 92(6); pp. 478-483; Dec. 1987.
Friede et al.; Accuracy of Cephalometric Prediction in Orthognathic Surgery; Journal of Oral and Maxillofacial Surgery; 45(9); pp. 754-760; Sep. 1987.

Friedrich et al; Measuring system for in vivo recording of force systems in orthodontic treatment-concept and analysis of accuracy; J. Biomech.; 32(1); pp. 81-85; (Abstract Only) Jan. 1999.
Futterling et al.; Automated Finite Element Modeling of a Human Mandible with Dental Implants; JS WSCG '98—Conference Program; 8 pages; retrieved from the Internet (https://dspace5.zcu.cz/bitstream/11025/15851/1/Strasser_98.pdf) on Aug. 21, 2018.
Gansky; Dental data mining: potential pitfalls and practical issues; Advances in Dental Research; 17(1); pp. 109-114; Dec. 2003.
Gao et al.; 3-D element Generation for Multi-Connected Complex Dental and Mandibular Structure; IEEE Proceedings International Workshop in Medical Imaging and Augmented Reality; pp. 267-271; Jun. 12, 2001.
Geomagic; Dental reconstruction; 1 page; retrieved from the internet (http://geomagic.comien/solutions/industry/detal_desc.php) on Jun. 6, 2008.
Gim-Alldent Deutschland, "Das DUX System: Die Technik," 3 pages; (English Translation Included); (year of pub. sufficiently earlier than effective US filing date and any foreign priority date); 2002.
Gottleib et al.; JCO Interviews Dr. James A. McNamura, Jr., on the Frankel Appliance: Part 2: Clinical 1-1 Management; Journal of Clinical Orthodontics; 16(6); pp. 390-407; retrieved from the internet (http://www.jco-online.com/archive/print_article.asp?Year=1982&Month=06&ArticleNum+); 21 pages; Jun. 1982.
Gottschalk et al.; OBBTree: A hierarchical structure for rapid interference detection; 12 pages; (http://www.cs.unc.edu/?geom/OBB/OBBT.html); retrieved from to internet (https://www.cse.iitk.ac.in/users/amit/courses/RMP/presentations/dslamba/presentation/sig96.pdf) on Apr. 25, 2019.
gpsdentaire.com; Get a realistic smile simulation in 4 steps with GPS; a smile management software; 10 pages; retrieved from the internet (http://www.gpsdentaire.com/en/preview/) on Jun. 6, 2008.
Grayson; New Methods for Three Dimensional Analysis of Craniofacial Deformity, Symposium: Computerized Facial Imaging in Oral and Maxillofacial Surgery; American Association of Oral and Maxillofacial Surgeons; 48(8) suppl 1; pp. 5-6; Sep. 13, 1990.
Grest, Daniel; Marker-Free Human Motion Capture in Dynamic Cluttered Environments from a Single View-Point, PhD Thesis; 171 pages; Dec. 2007.
Guess et al.; Computer Treatment Estimates in Orthodontics and Orthognathic Surgery; Journal of Clinical Orthodontics; 23(4); pp. 262-268; 11 pages; (Author Manuscript); Apr. 1989.
Heaven et al.; Computer-Based Image Analysis of Artificial Root Surface Caries; Abstracts of Papers #2094; Journal of Dental Research; 70:528; (Abstract Only); Apr. 17-21, 1991.
Highbeam Research; Simulating stress put on jaw. (ANSYS Inc.'s finite element analysis software); 2 pages; retrieved from the Internet (http://static.highbeam.eom/t/toolingampproduction/november011996/simulatingstressputonfa..); on Nov. 5, 2004.
Hikage; Integrated Orthodontic Management System for Virtual Three-Dimensional Computer Graphic Simulation and Optical Video Image Database for Diagnosis and Treatment Planning; Journal of Japan KA Orthodontic Society; 46(2); pp. 248-269; 56 pages; (English Translation Included); Feb. 1987.
Hoffmann et al.; Role of Cephalometry for Planning of Jaw Orthopedics and Jaw Surgery Procedures; Informatbnen, pp. 375-396; (English Abstract Included); Mar. 1991.
Hojjatie et al.; Three-Dimensional Finite Element Analysis of Glass-Ceramic Dental Crowns; Journal of Biomechanics; 23(11); pp. 1157-1166; Jan. 1990.
Huckins; CAD-CAM Generated Mandibular Model Prototype from MRI Data; AAOMS, p. 96; (Abstract Only); (year of pub. sufficiently earlier than effective US filed and any foreign priority date) 1999.
Invisalign; You were made to move. There's never been a better time to straighten your teeth with the most advanced clear aligner in the world; Product webpage; 2 pages; retrieved from the internet (www.invisalign.com/) on Dec. 28, 2017.
JCO Interviews; Craig Andreiko , DDS, MS on the Elan and Orthos Systems; Interview by Dr. Larry W. White; Journal of Clinical Orthodontics; 28(8); pp. 459-468; 14 pages; (Author Manuscript); Aug. 1994.

(56) References Cited

OTHER PUBLICATIONS

JCO Interviews; Dr. Homer W. Phillips on Computers in Orthodontic Practice, Part 2; Journal of Clinical Orthodontics; 17(12); pp. 819-831; 19 pages; (Author Manuscript); Dec. 1983.
Jerrold; The Problem, Electronic Data Transmission and the Law; American Journal of Orthodontics and Dentofacial Orthopedics; 113(4); pp. 478-479; 5 pages; (Author Manuscript); Apr. 1998.
Jones et al.; An Assessment of the Fit of a Parabolic Curve to Pre- and Post-Treatment Dental Arches; British Journal of Orthodontics; 16(2); pp. 85-93; May 1989.
Kamada et.al.; Case Reports on Tooth Positioners Using LTV Vinyl Silicone Rubber; J. Nihon University School of Dentistry; 26(1); pp. 11-29; (year of pub. sufficiently earlier than effective US filing date and any foreign priority date) 1984.
Kamada et.al.; Construction of Tooth Positioners with LTV Vinyl Silicone Rubber and Some Case KJ Reports; J. Nihon University School of Dentistry; 24(1); pp. 1-27; (year of pub. sufficiently earlier than effective US filing date and any foreign priority date) 1982.
Kanazawa et al.; Three-Dimensional Measurements of the Occlusal Surfaces of Upper Molars in a Dutch Population; Journal of Dental Research; 63(11); pp. 1298-1301; Nov. 1984.
Karaman et al.; A practical method of fabricating a lingual retainer; Am. Journal of Orthodontic and Dentofacial Orthopedics; 124(3); pp. 327-330; Sep. 2003.
Kesling et al.; The Philosophy of the Tooth Positioning Appliance; American Journal of Orthodontics and Oral surgery; 31(6); pp. 297-304; Jun. 1945.
Kesling; Coordinating the Predetermined Pattern and Tooth Positioner with Conventional Treatment; American Journal of Orthodontics and Oral Surgery; 32(5); pp. 285-293; May 1946.
Kleeman et al.; The Speed Positioner; J. Clin. Orthod.; 30(12); pp. 673-680; Dec. 1996.
Kochanek; Interpolating Splines with Local Tension, Continuity and Bias Control; Computer Graphics; 18(3); pp. 33-41; Jan. 1, 1984.
Kunii et al.; Articulation Simulation for an Intelligent Dental Care System; Displays; 15(3); pp. 181-188; Jul. 1994.
Kuroda et al.; Three-Dimensional Dental Cast Analyzing System Using Laser Scanning; American Journal of Orthodontics and Dentofacial Orthopedics; 110(4); pp. 365-369; Oct. 1996.
Laurendeau et al.; A Computer-Vision Technique for the Acquisition and Processing of 3-D Profiles of 7 Dental Imprints: An Application in Orthodontics; IEEE Transactions on Medical Imaging; 10(3); pp. 453-461; Sep. 1991.
Leinfelder et al.; A New Method for Generating Ceramic Restorations: a CAD-CAM System; Journal of the American Dental Association; 118(6); pp. 703-707; Jun. 1989.
Manetti et al.; Computer-Aided Cefalometry and New Mechanics in Orthodontics; Fortschr Kieferorthop; 44; pp. 370-376; 8 pages.; (English Article Summary Included); (year of pub. sufficiently earlier than effective US filing date and any foreign priority date) 1983.
McCann; Inside the ADA; J. Amer. Dent. Assoc, 118:286-294; Mar. 1989.
McNamara et al.; Invisible Retainers; J. Clin Orthod.; pp. 570-578; 11 pages; (Author Manuscript); Aug. 1985.
McNamara et al.; Orthodontic and Orthopedic Treatment in the Mixed Dentition; Needham Press; pp. 347-353; Jan. 1993.
Methot; Get the picture with a gps for smile design in 3 steps; Spectrum; 5(4); pp. 100-105; (year of pub. sufficiently earlier than effective US filing date and any foreign priority date) 2006.
Moermann et al, Computer Machined Adhesive Porcelain Inlays: Margin Adaptation after Fatigue Stress; IADR Abstract 339; J. Dent. Res.; 66(a):763; (Abstract Only); (year of pub. sufficiently earlier than effective US filing date and any foreign priority date) 1987.
Moles; Correcting Mild Malalignments—As Easy as One, Two, Three; AOA/Pro Corner; 11(2); 2 pages; (year of pub. sufficiently earlier than effective US filing date and any foreign priority date) 2002.
Mormann et al.; Marginale Adaptation von adhasuven Porzellaninlays in vitro; Separatdruck aus:Schweiz. Mschr. Zahnmed.; 95; pp. 1118-1129; 8 pages; (Machine Translated English Abstract); (year of pub. sufficiently earlier than effective US filing date and any foreign priority date); 1985.
Nahoum; The Vacuum Formed Dental Contour Appliance; N. Y. State Dent. J.; 30(9); pp. 385-390; Nov. 1964.
Nash; CEREC CAD/CAM Inlays: Aesthetics and Durability in a Single Appointment; Dentistry Today; 9(8); pp. 20, 22-23 and 54; Oct. 1990.
Newcombe; DTAM: Dense tracking and mapping in real-time; 8 pages; retrieved from the internet (http://www.dock.ac.ukriajd/Publications/newcombe_etal_iccv2011.pdf; on Dec. 2011.
Nishiyama et al.; A New Construction of Tooth Repositioner by LTV Vinyl Silicone Rubber; The Journal of Nihon University School of Dentistry; 19(2); pp. 93-102 (year of pub. sufficiently earlier than effective US filing date and any foreign priority date) 1977.
Ogawa et al.; Mapping, profiling and clustering of pressure pain threshold (PPT) in edentulous oral muscosa; Journal of Dentistry; 32(3); pp. 219-228; Mar. 2004.
Ogimoto et al.; Pressure-pain threshold determination in the oral mucosa; Journal of Oral Rehabilitation; 29(7); pp. 620-626; Jul. 2002.
ormco.com; Increasing clinical performance with 3D interactive treatment planning and patient-specific appliances; 8 pages; retrieved from the Internet (http://www.konsident.com/wp-content/files_mf/1295385693http_ormco.com_index_cmsfilesystemaction_fileOrmcoPDF_whitepapers.pdf) on Feb. 27, 2019.
OrthoCAD downloads; retrieved Jun. 27, 2012 from the internet (www.orthocad.com/download/downloads.asp); 2 pages; Feb. 14, 2005.
Page et al.; Validity and accuracy of a risk calculator in predicting periodontal disease; Journal of the American Dental Association; 133(5); pp. 569-576; May 2002.
Patterson Dental; Cosmetic imaging; 2 pages retrieved from the internet (http://patterson.eaglesoft.net/cnt_di_cosimg.html) on Jun. 6, 2008.
Paul et al.; Digital Documentation of Individual Human Jaw and Tooth Forms for Applications in Orthodontics; Oral Surgery and Forensic Medicine Proc. of the 24th Annual Conf. of the IEEE Industrial Electronics Society (IECON '98); vol. 4; pp. 2415-2418; Sep. 4, 1998.
Pinkham; Foolish Concept Propels Technology; Dentist, 3 pages , Jan./Feb. 1989.
Pinkham; Inventor's CAD/CAM May Transform Dentistry; Dentist; pp. 1 and 35, Sep. 1990.
Ponitz; Invisible retainers; Am. J. Orthod.; 59(3); pp. 266-272; Mar. 1971.
Procera Research Projects; Procera Research Projects 1993 Abstract Collection; 23 pages; (year of pub. sufficiently earlier than effective US filing date and any foreign priority date) 1993.
Proffit et al.; The first stage of comprehensive treatment alignment and leveling; Contemporary Orthodontics, 3rd Ed.; Chapter 16; Mosby Inc.; pp. 534-537; (year of pub. sufficiently earlier than effective US filing date and any foreign priority date) 2000.
Proffit et al.; The first stage of comprehensive treatment: alignment and leveling; Contemporary Orthodontics; (Second Ed.); Chapter 15, MosbyYear Book; St. Louis, Missouri; pp. 470-533 Oct. 1993.
Raintree Essix & ARS Materials, Inc., Raintree Essix, Technical Magazine Table of contents and Essix Appliances, 7 pages; retrieved from the internet (http://www.essix.com/magazine/defaulthtml) on Aug. 13, 1997.
Redmond et al.; Clinical Implications of Digital Orthodontics; American Journal of Orthodontics and Dentofacial Orthopedics; 117(2); pp. 240-242; Feb. 2000.
Rekow et al.; CAD/CAM for Dental Restorations—Some of the Curious Challenges; IEEE Transactions on Biomedical Engineering; 38(4); pp. 314-318; Apr. 1991.
Rekow et al.; Comparison of Three Data Acquisition Techniques for 3-D Tooth Surface Mapping; Annual International Conference of the IEEE Engineering in Medicine and Biology Society; 13(1); pp.

(56) References Cited

OTHER PUBLICATIONS 344-345 (year of pub. sufficiently earlier than effective US filing date and any foreign priority date) 1991.

Rekow; A Review of the Developments in Dental CAD/CAM Systems; Current Opinion in Dentistry; 2; pp. 25-33; Jun. 1992.

Rekow; CAD/CAM in Dentistry: A Historical Perspective and View of the Future; Journal Canadian Dental Association; 58(4); pp. 283, 287-288; Apr. 1992.

Rekow; Computer-Aided Design and Manufacturing in Dentistry: A Review of the State of the Art; Journal of Prosthetic Dentistry; 58(4); pp. 512-516; Dec. 1987.

Rekow; Dental CAD-CAM Systems: What is the State of the Art?; The Journal of the American Dental Association; 122(12); pp. 43-48; Dec. 1991.

Rekow; Feasibility of an Automated System for Production of Dental Restorations, Ph.D. Thesis; Univ. of Minnesota, 250 pages, Nov. 1988.

Richmond et al.; The Development of the PAR Index (Peer Assessment Rating): Reliability and Validity.; The European Journal of Orthodontics; 14(2); pp. 125-139; Apr. 1992.

Richmond et al.; The Development of a 3D Cast Analysis System; British Journal of Orthodontics; 13(1); pp. 53-54; Jan. 1986.

Richmond; Recording the Dental Cast in Three Dimensions; American Journal of Orthodontics and Dentofacial Orthopedics; 92(3); pp. 199-206; Sep. 1987.

Rubin et al.; Stress analysis of the human tooth using a three-dimensional finite element model; Journal of Dental Research; 62(2); pp. 82-86; Feb. 1983.

Rudge; Dental Arch Analysis: Arch Form, A Review of the Literature; The European Journal of Orthodontics; 3(4); pp. 279-284; Jan. 1981.

Sahm et al.; "Micro-Electronic Monitoring of Functional Appliance Wear"; Eur J Orthod.; 12(3); pp. 297-301; Aug. 1990.

Sahm; Presentation of a wear timer for the clarification of scientific questions in orthodontic orthopedics; Fortschritte der Kieferorthopadie; 51 (4); pp. 243-247; (Translation Included) Jul. 1990.

Sakuda et al.; Integrated Information-Processing System in Clinical Orthodontics: An Approach with Use of a Computer Network System; American Journal of Orthodontics and Dentofacial Orthopedics; 101(3); pp. 210-220; 20 pages; (Author Manuscript) Mar. 1992.

Schellhas et al.; Three-Dimensional Computed Tomography in Maxillofacial Surgical Planning; Archives of Otolaryngology—Head and Neck Surgery; 114(4); pp. 438-442; Apr. 1988.

Schroeder et al; Eds. The Visual Toolkit, Prentice Hall PTR, New Jersey; Chapters 6, 8 & 9, (pp. 153-210,309-354, and 355-428; (year of pub. sufficiently earlier than effective US filing date and any foreign priority date) 1998.

Shilliday; Minimizing finishing problems with the mini-positioner; American Journal of Orthodontics; 59(6); pp. 596-599; Jun. 1971.

Siemens; CEREC—Computer-Reconstruction, High Tech in der Zahnmedizin; 15 pagesl; (Includes Machine Translation); (year of pub. sufficiently earlier than effective US filing date and any foreign priority date); 2004.

Sinclair; The Readers' Corner; Journal of Clinical Orthodontics; 26(6); pp. 369-372; 5 pages; retrived from the internet (http://www.jco-online.com/archive/print_article.asp?Year=1992&Month=06&ArticleNum=); Jun. 1992.

Sirona Dental Systems GmbH, CEREC 3D, Manuel utiiisateur, Version 2.0X (in French); 114 pages; (English translation of table of contents included); (year of pub. sufficiently earlier than effective US filing date and any foreign priority date); 2003.

Smart Technology; Smile library II; 1 page; retrieved from the internet (http://smart-technology.net/) on Jun. 6, 2008.

Smile-Vision_The smile-vision cosmetic imaging system; 2 pages; retrieved from the internet (http://www.smile-vision.net/cos_imaging.php) on Jun. 6, 2008.

Stoll et al.; Computer-aided Technologies in Dentistry; Dtsch Zahna'rztl Z 45, pp. 314-322; (English Abstract Included); (year of pub. sufficiently earlier than effective US filing date and any foreign priority date) 1990.

Sturman; Interactive Keyframe Animation of 3-D Articulated Models; Proceedings Graphics Interface '84; vol. 86; pp. 35-40; May-Jun. 1984.

Szeliski; Introduction to computer vision: Structure from motion; 64 pages; retrieved from the internet (http://robots.stanford.edu/cs223b05/notes/CS%20223-B%20L10%structurefrommotion1b.ppt, on Feb. 3, 2005.

The American Heritage, Stedman's Medical Dictionary; Gingiva; 3 pages; retrieved from the interent (http://reference.com/search/search?q=gingiva) on Nov. 5, 2004.

Thera Mon; "Microsensor"; 2 pages; retrieved from the internet (www.english.thera-mon.com/the-product/transponder/index.html); on Sep. 19, 2016.

Thorlabs; Pellin broca prisms; 1 page; retrieved from the internet (www.thorlabs.com); Nov. 30, 2012.

Tiziani et al.; Confocal principle for macro and microscopic surface and defect analysis; Optical Engineering; 39(1); pp. 32-39; Jan. 1, 2000.

Truax; Truax Clasp-Less(TM) Appliance System; The Functional Orthodontist; 9(5); pp. 22-24, 26-28; Sep.-Oct. 1992.

Tru-Tatn Orthodontic & Dental Supplies, Product Brochure, Rochester, Minnesota 55902, 16 pages; (year of pub. sufficiently earlier than effective US filing date and any foreign priority date) 1996.

U.S. Department of Commerce, National Technical Information Service, Holodontography: An Introduction to Dental Laser Holography; School of Aerospace Medicine Brooks AFB Tex; Mar. 1973, 40 pages; Mar. 1973.

U.S. Department of Commerce, National Technical Information Service; Automated Crown Replication Using Solid Photography SM; Solid Photography Inc., Melville NY,; 20 pages; Oct. 1977.

Vadapalli; Minimum intensity projection (MinIP) is a data visualization; 7 pages; retrieved from the internet (https://prezi.com/tdmttnmv2knw/minimum-intensity-projection-minip-is-a-data-visualization/) on Sep. 6, 2018.

Van Der Linden et al.; Three-Dimensional Analysis of Dental Casts by Means of the Optocom; Journal of Dental Research; 51(4); p. 1100; Jul.-Aug. 1972.

Van Der Linden; A New Method to Determine Tooth Positions and Dental Arch Dimensions; Journal of Dental Research; 51(4); p. 1104; Jul.-Aug. 1972.

Van Der Zel; Ceramic-Fused-to-Metal Restorations with a New CAD/CAM System; Quintessence International; 24(A); pp. 769-778; (year of pub. sufficiently earlier than effective US filing date and any foreign priority date); 1993.

Varady et al.; Reverse Engineering of Geometric Models An Introduction; Computer-Aided Design; 29(4); pp. 255-268; 20 pages; (Author Manuscript); Apr. 1997.

Verstreken et al.; An Image-Guided Planning System for Endosseous Oral Implants; IEEE Transactions on Medical Imaging; 17(5); pp. 842-852; Oct. 1998.

Vevin et al.; Pose estimation of teeth through crown-shape matching; In Medical Imaging: Image Processing of International Society of Optics and Photonics; vol. 4684; pp. 955-965; May 9, 2002.

Video of DICOM to Surgical Guides; Can be viewed at <URL:https://youtu.be/47KtOmCEFQk; Published Apr. 4, 2016.

Virtual Orthodontics; Our innovative software; 2 pages; (http://www.virtualorthodontics.com/innovativesoftware.html); retrieved from the internet (https://web.archive.org/web/20070518085145/http://www.virtualorthodontics.com/innovativesoftware.html); (year of pub. sufficiently earlier than effective US filing date and any foreign priority date) 2005.

Warunek et al.; Physical and Mechanical Properties of Elastomers in Orthodonic Positioners; American Journal of Orthodontics and Dentofacial Orthopedics; 95(5); pp. 388-400; 21 pages; (Author Manuscript); May 1989.

Warunek et.al.; Clinical Use of Silicone Elastomer Applicances; JCO; 23(10); pp. 694-700; Oct. 1989.

(56) References Cited

OTHER PUBLICATIONS

Watson et al.; Pressures recorded at to denture base-mucosal surface interface in complete denture wearers; Journal of Oral Rehabilitation 14(6); pp. 575-589; Nov. 1987.
Wells; Application of the Positioner Appliance in Orthodontic Treatment; American Journal of Orthodontics; 58(4); pp. 351-366; Oct. 1970.
Wiedmann; According to the laws of harmony to find the right tooth shape with assistance of the computer; Digital Dental News; 2nd Vol.; pp. 0005-0008; (English Version Included); Apr. 2008.
Wikipedia; Palatal expansion; 3 pages; retrieved from the internet (https://en.wikipedia.org/wiki/Palatal_expansion) on Mar. 5, 2018.
Williams; Dentistry and CAD/CAM: Another French Revolution; J. Dent. Practice Admin.; 4(1); pp. 2-5 Jan./Mar. 1987.
Williams; The Switzerland and Minnesota Developments in CAD/CAM; Journal of Dental Practice Administration; 4(2); pp. 50-55; Apr./Jun. 1987.
Wishan; New Advances in Personal Computer Applications for Cephalometric Analysis, Growth Prediction, Surgical Treatment Planning and Imaging Processing; Symposium: Computerized Facial Imaging in Oral and Maxilofacial Surgery; p. 5; Presented on Sep. 13, 1990.
Witt et al.; The wear-timing measuring device in orthodontics-cui bono? Reflections on the state-of-the-art in wear-timing measurement and compliance research in orthodontics; Fortschr Kieferorthop.; 52(3); pp. 117-125; (Translation Included) Jun. 1991.
Wolf; Three-dimensional structure determination of semi-transparent objects from holographic data; Optics Communications; 1(4); pp. 153-156; Sep. 1969.
Wong et al.; The uses of orthodontic study models in diagnosis and treatment planning; Hong Knog Dental Journal; 3(2); pp. 107-115; Dec. 2006.
WSCG'98—Conference Program, The Sixth International Conference in Central Europe on Computer Graphics and Visualization '98; pp. 1-7; retrieved from the Internet on Nov. 5, 2004, (http://wscg.zcu.cz/wscg98/wscg98.htm); Feb. 9-13, 1998.
Xia et al.; Three-Dimensional Virtual-Reality Surgical Planning and Soft-Tissue Prediction for Orthognathic Surgery; IEEE Transactions on Information Technology in Biomedicine; 5(2); pp. 97-107; Jun. 2001.
Yaltara Software; Visual planner; 1 page; retrieved from the internet (http://yaltara.com/vp/) on Jun. 6, 2008.
Yamada et al.; Simulation of fan-beam type optical computed-tomography imaging of strongly scattering and weakly absorbing media; Applied Optics; 32(25); pp. 4808-4814; Sep. 1, 1993.
Yamamoto et al.; Optical Measurement of Dental Cast Profile and Application to Analysis of Three-Dimensional Tooth Movement in Orthodontics; Front. Med. Biol. Eng., 1(2); pp. 119-130; (year of pub. sufficiently earlier than effective US filing date and any foreign priority date); 1988.
Yamamoto et al.; Three-Dimensional Measurement of Dental Cast Profiles and Its Applications to Orthodontics; Conf. Proc. IEEE Eng. Med. Biol. Soc.; 12(5); pp. 2052-2053; Nov. 1990.
Yamany et al.; A System for Human Jaw Modeling Using Intra-Oral Images; Proc. of the 20th Annual Conf. of the IEEE Engineering in Medicine and Biology Society; vol. 2; pp. 563-566; Oct. 1998.
Yoshii; Research on a New Orthodontic Appliance: The Dynamic Positioner (D.P.); 111. The General Concept of the D.P. Method and Its Therapeutic Effect, Part 1, Dental and Functional Reversed Occlusion Case Reports; Nippon Dental Review; 457; pp. 146-164; 43 pages; (Author Manuscript); Nov. 1980.
Yoshii; Research on a New Orthodontic Appliance: The Dynamic Positioner (D.P.); I. The D.P. Concept and Implementation of Transparent Silicone Resin (Orthocon); Nippon Dental Review; 452; pp. 61-74; 32 pages; (Author Manuscript); Jun. 1980.
Yoshii; Research on a New Orthodontic Appliance: The Dynamic Positioner (D.P.); II. The D.P. Manufacturing Procedure and Clinical Applications; Nippon Dental Review; 454; pp. 107-130; 48 pages; (Author Manuscript); Aug. 1980.

Yoshii; Research on a New Orthodontic Appliance: The Dynamic Positioner (D.P.); III—The General Concept of the D.P. Method and Its Therapeutic Effect, Part 2. Skeletal Reversed Occlusion Case Reports; Nippon Dental Review; 458; pp. 112-129; 40 pages; (Author Manuscript); Dec. 1980.
Zhang et al.; Visual speech features extraction for improved speech recognition; 2002 IEEE International conference on Acoustics, Speech and Signal Processing; vol. 2; 4 pages; May 13-17, 2002.
Morton et al.; U.S. Appl. No. 16/177,067 entitled "Dental appliance having selective occlusal loading and controlled intercuspation," filed Oct. 31, 2018.
Akopov et al.; U.S. Appl. No. 16/178,491 entitled "Automatic treatment planning," filed Nov. 1, 2018.
O'Leary et al.; U.S. Appl. No. 16/195,701 entitled "Orthodontic retainers," filed Nov. 19, 2018.
Shanjani et al., U.S. Appl. No. 16/206,894 entitled "Sensors for monitoring oral appliances," filed Nov. 28, 2019.
Shanjani et al., U.S. Appl. No. 16/231,906 entitled "Augmented reality enhancements for dental practitioners." Dec. 24, 2018.
Kopleman et al., U.S. Appl. No. 16/220,381 entitled "Closed loop adaptive orthodontic treatment methods and apparatuses," Dec. 14, 2018.
Sabina et al., U.S. Appl. No. 16/258,516 entitled "Diagnostic intraoral scanning" filed Jan. 25, 2019.
Sabina et al., U.S. Appl. No. 16/258,523 entitled "Diagnostic intraoral tracking" filed Jan. 25, 2019.
Sabina et al., U.S. Appl. No. 16/258,527 entitled "Diagnostic intraoral methods and apparatuses" filed Jan. 25, 2019.
Li et al.; U.S. Appl. No. 16/171,159 entitled "Alternative bite adjustment structures," filed Oct. 25, 2018.
Culp; U.S. Appl. No. 16/236,220 entitled "Laser cutting," filed Dec. 28, 2018.
Culp; U.S. Appl. No. 16/265,287 entitled "Laser cutting," filed Feb. 1, 2019.
Arnone et al.; U.S. Appl. No. 16/235,449 entitled "Method and system for providing indexing and cataloguing of orthodontic related treatment profiles and options," filed Dec. 28, 2018.
Mason et al.; U.S. Appl. No. 16/374,648 entitled "Dental condition evaluation and treatment," filed Apr. 3, 2019.
Brandt et al.; U.S. Appl. No. 16/235,490 entitled "Dental wire attachment," filed Dec. 28, 2018.
Kou; U.S. Appl. No. 16/270,891 entitled "Personal data file," filed Feb. 8, 2019.
Bernabe et al.; Are the lower incisors the best predictors for the unerupted canine and premolars sums? An analysis of peruvian sample; The Angle Orthodontist; 75(2); pp. 202-207; Mar. 2005.
Collins English Dictionary; Teeth (definition); 9 pages; retrieved from the internet (https:www.collinsdictionary.com/us/dictionary/english/teeth) on May 13, 2019.
dictionary.com; Plural (definition); 6 pages; retrieved from the internet ( https://www.dictionary.com/browse/plural#) on May 13, 2019.
dictionary.com; Quadrant (definition); 6 pages; retrieved from the internet ( https://www.dictionary.com/browse/quadrant?s=t) on May 13, 2019.
Martinelli et al.; Prediction of lower permanent canine and premolars width by correlation methods; The Angle Orthodontist; 75(5); pp. 805-808; Sep. 2005.
Nourallah et al.; New regression equations for predicting the size of unerupted canines and premolars in a contemporary population; The Angle Orthodontist; 72(3); pp. 216-221; Jun. 2002.
Paredes et al.; A new, accurate and fast digital method to predict unerupted tooth size; The Angle Orthodontist; 76(1); pp. 14-19; Jan. 2006.
Dental Monitoring; Basics: How to put the cheek retractor?; 1 page (Screenshot); retrieved from the interenet (https://www.youtube.com/watch?y=6K1HXw4Kq3c); May 27, 2016.
Dental Monitoring; Dental monitoring tutorial; 1 page (Screenshot); retrieved from the internet (https:www.youtube.com/watch?v=Dbe3udOf9_c); Mar. 18, 2015.
Ecligner Selfie; Change your smile; 1 page (screenshot); retrieved from the internet (https:play.google.com/store/apps/details?id=parklict.ecligner); on Feb. 13, 2018.

(56) References Cited

OTHER PUBLICATIONS

Lawrence; Salivary markers of systemic disease: noninvasive diagnosis of disease and monitoring of general health; Journal of the Canadian Dental Association Clinical Practice; 68(3); pp. 170-174; Mar. 2002.

Nishanian et al.; Oral fluids as an alternative to serum for measurement of markers of immune activation; Clinical and Diagnostic Laboratory Immunology; 5(4); pp. 507-512; Jul. 1998.

Svec et al.; Molded rigid monolithic porous polymers: an inexpensive, efficient, and versatile alternative to beads for design of materials for numerous applications; Industrial and Engineering Chemistry Research; 38(1); pp. 34-48; Jan. 4, 1999.

U.S. Food and Drug Administration; Color additives; 3 pages; retrieved from the Internet (https://websrchive.org/web/20070502213911/http://www.cfsan.fda.gov/~dms/col-toc.html); last known as May 2, 2007.

Chen et al.; U.S. Appl. No. 16/223,019 entitled "Release agent receptacle," filed Dec. 17, 2018.

* cited by examiner

DENTAL IMPLANT POSITIONING

CROSS-REFERENCE TO RELATED APPLICATIONS

This application is a continuation of U.S. patent application Ser. No. 12/154,526, filed May 23, 2008, now U.S. Pat. No. 9,492,243, the contents of which are hereby incorporated by reference.

BACKGROUND

The present disclosure is related generally to the field of dental treatments. More particularly, the present disclosure is related to using a dental positioning appliance to facilitate dental implant positioning.

Some dental processes use positioning appliances for realigning teeth. Such appliances may utilize a thin shell of material having resilient properties, referred to as an "aligner", which generally conforms to a patient's teeth but is slightly out of alignment with the initial tooth configuration.

Placement of such an appliance over the teeth provides controlled forces in specific locations to gradually move the teeth into a new configuration. Repetition of this process with successive appliances that provide progressive repositioning may eventually move the teeth through a series of intermediate arrangements to a final desired arrangement, which then may allow positioning of the dental implant to occur at that time.

Some dental treatments involve a combination of repositioning misaligned teeth and insertion of a dental implant for improved cosmetic appearance and/or dental function. Repositioning of teeth may result from inadequate space to access a desired implant position and/or a desire to provide an improved position for placement of the implant by aligning neighboring teeth.

Repositioning may be accomplished, for instance, by applying orthodontic forces to one or more teeth over a period of time. This may be performed, in some instances, by first aligning the teeth using dental braces, and then placing the implant when the desired implant position has been adequately prepared.

This approach may be beneficial in many instances. However, such a dental treatment sequence may prolong the therapeutic regimen by waiting until dental realignment is complete before initiating positioning of the implant. Potential drawbacks also may include compromised smile appearance when the implant position is in an anterior region of the mouth and/or risks known to be associated with treatments using dental braces, among others.

DETAILED DESCRIPTION

Figures 1A, 1B:
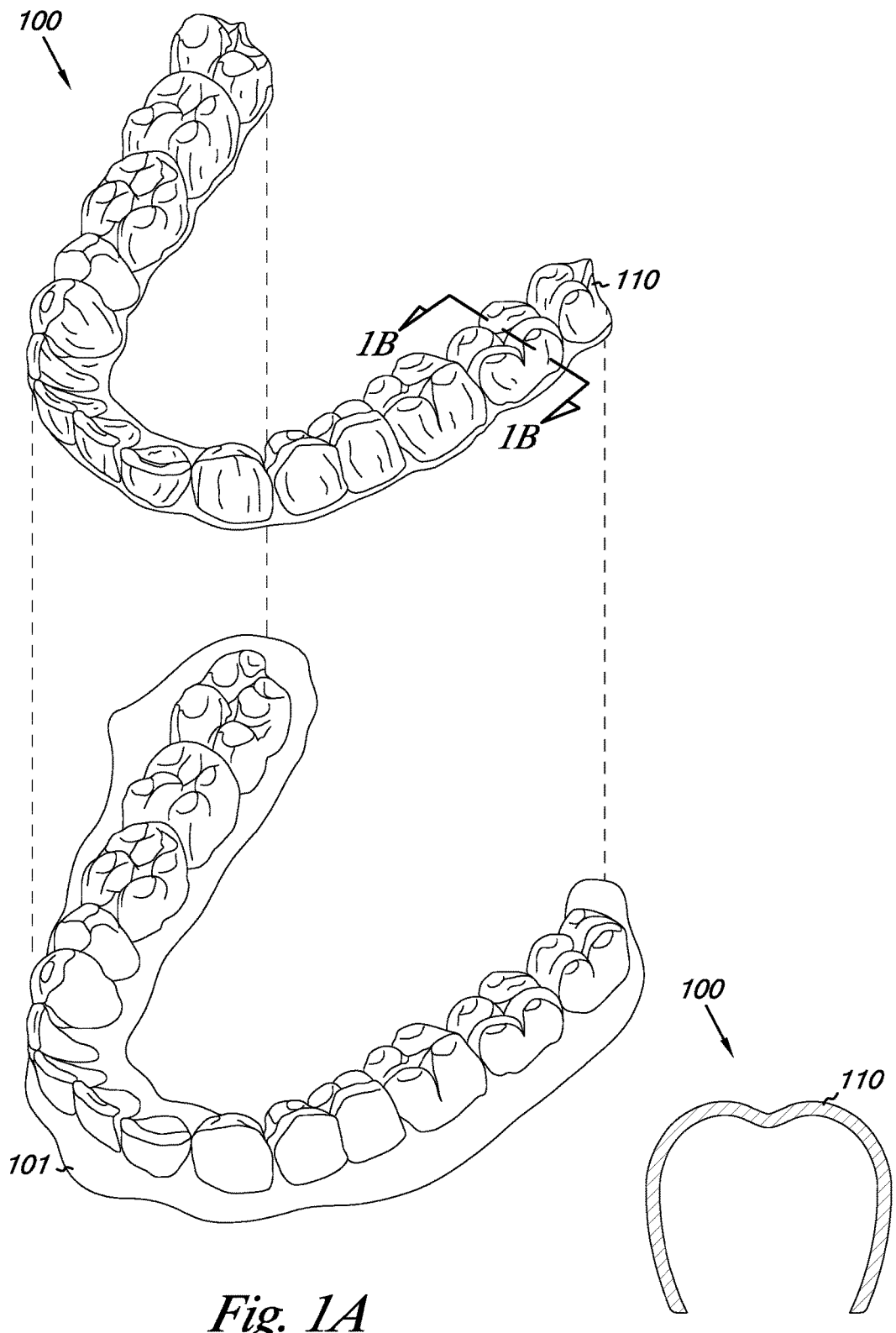
FIG. 1A illustrates a lower jaw of a patient together with an example of a dental positioning adjustment appliance.
FIG. 1B illustrates a cut away view of the appliance of FIG. 1A taken along line 1B-1B.

In some dental procedures, a computerized tomography (CT) scan may be created to define a patient's dentition prior to initiation of dental implant treatment. In some such procedures, a virtual implant may be placed on the scan during the planning process in a simulated implant treatment position to help avoid impingement of the implant on important anatomical structures (e.g., nerves, blood vessels, and/or adjacent tooth roots) and also to plan a desired position of the implant in the bone to improve osseointegration in the actual implant. The virtual implant also may be positioned in a way that provides an implant surgeon and/or dentist improved access to the implant when restoring the implant with a final prosthetic (e.g., a crown, overdenture, etc.).

As used herein, the term implant can include permanent implants or temporary implants (e.g., mini implants or temporary anchorage devices). Positioning of the implant (both virtual and actual) may, however, be compromised when one or more of the patient's teeth are originally in such a position so as to obstruct a desired placement of the implant. For instance, angulation of adjacent teeth to a desired implant position may be such that a line of draw for restoring the implant may compromise the access and/or retention of the prosthesis to the implant.

Another possibility may be that the angulation between the implant and the final restoration is undesirable due to resulting loading characteristics when the implant is restored. A further possibility, among others, is that a bite relationship (e.g., occlusion) between the lower and upper jaw may be such that resulting forces on the placed implant would be unfavorable for long-term success of the implant.

In such instances, the existing positioning of the surrounding teeth (including those in the opposing jaw) may not provide a favorable and/or desirable dental occlusion and/or cosmetic appearance for placement of dental implants. That is, an alternative position of the teeth and/or jaw relationship may provide a more favorable arrangement for successful prognosis for placement of one or more implants. A determination of a more favorable occlusion based on repositioning of tooth arrangement and/or jaw position may enable an improved position of the dental implant, for example, when obstructing and/or interfering teeth are repositioned into the desired position, according to the treatment plan, prior to implant placement.

According to the present disclosure, appliances and methods are provided for positioning an implant with dental treatment by determining an implant location based on a virtual model of an optimized dental occlusion. Among the various embodiments described herein, one or more teeth can be moved using a first number of a series of dental appliances from a first orientation to a second orientation, where the second orientation exposes the implant location, and an implant can be placed at the exposed implant location using a landmark included in at least one of the series of dental appliances. One or more teeth can, in various embodiments, be repositioned using a second number of the series of dental appliances, from the second orientation to a successive orientation.

FIG. 1A illustrates a lower jaw of a patient together with an example of a dental positioning adjustment appliance. As described in the present disclosure, embodiments of dental positioning adjustment appliances, as illustrated in FIG. 1A, can include an appliance 100 made out of a polymeric material 110. However, the appliance 100 made out of the polymeric material 110 is presented by way of example and not by way of limitation.

That is, appliances used for dental positioning adjustment (which, as described in the present disclosure, can be termed "aligners") can be formed using a variety of techniques and remain consistent with the present disclosure. The polymeric material can be a planar sheet of material or strips of material, among other material configurations.

The methods of the present disclosure can employ any positioners, retainers, and/or other removable appliances for finishing and/or maintaining teeth positions in connection with dental treatment. The embodiments of the present disclosure can provide a plurality of such appliances intended, for example, to be worn by a patient successively in order to achieve the gradual tooth repositioning, as described herein.

The appliance 100 can, for example, be formed from a polymeric shell having a cavity shaped to receive and resiliently reposition one or more teeth from one teeth arrangement to a successive teeth arrangement. The polymeric shell may be designed to fit over a number of teeth (e.g., all teeth, as illustrated in FIG. 1A) present in the upper and/or lower jaw 101 of a patient.

In some situations, certain individual and/or sets of teeth can be repositioned while other teeth can provide a base and/or anchor region for holding the repositioning appliance in place as it applies the resilient repositioning force against the tooth or teeth to be repositioned. In complex cases, however, many or most of the teeth will be repositioned at some point during the treatment. In such cases, one or more of the teeth to be moved also can serve as a base and/or anchor region for holding the repositioning appliance.

Additionally, the gums (e.g., the gingiva), the palate, and/or other surrounding tissue can contribute to serving as an anchor region, thus allowing all or nearly all of the teeth to be repositioned at the same time. In some cases, however, individual attachments may be affixed on one or more of the teeth with corresponding receptacles or apertures in the appliance 100, as described in detail in with regard to other figures in the present disclosure.

FIG. 1B illustrates a cut away view of the appliance of FIG. 1A taken along line 1B-1B. The cut away view of the appliance 100 illustrated in FIG. 1B illustrates an embodiment made out of a polymeric material 110 included, for example, in a polymeric shell having a cavity shaped to receive and resiliently reposition one or more teeth from one teeth arrangement to a successive teeth arrangement.

Among the considerations to be resolved following dental treatment as just described may be precisely where to position the implants because, for instance, the CT-aided implant placement determined prior to the dental treatment may not account for tooth movement that occurs during the dental treatment. That is, the CT-aided implant placement may determine an appropriate position for the implants in the current arrangement of the dentition, rather than after repositioning of a number of teeth during the orthodontic dental treatment.

Positioning of dental implants as a surgical procedure after the orthodontic dental treatment may introduce alterations in the dentition position, the root position, and/or the surrounding gingival and/or alveolar bone structure that may affect the prognosis of the subsequent implant placement. Another consideration may be implant treatments being static, for instance, when the implants may be placed on the teeth as they originally reside, when some tooth movement prior to placement of the implant, in some situations, could result in a superior functional and/or aesthetic result.

Figure 2A:
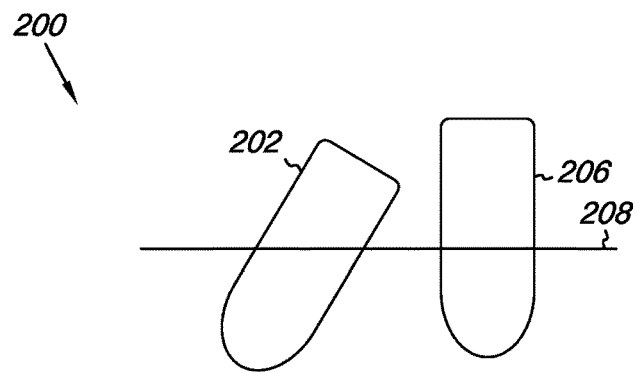
FIG. 2A illustrates an example of misaligned teeth in a lower jaw of a patient with inadequate space for a final restoration supported by a dental implant.

FIG. 2A illustrates an example of misaligned teeth in a lower jaw of a patient with inadequate space for a final restoration supported by a dental implant. The example of misaligned teeth 200 illustrated in FIG. 2A shows one improperly oriented tooth 202 adjacent to one substantially properly oriented tooth 206. The one improperly oriented tooth 202 and the one substantially properly oriented tooth 206 are shown to be positioned in a substrate 208 that can, in various embodiments, represent a gum line or a jaw bone.

The example illustrated in FIG. 2A shows a vacancy between the one improperly oriented tooth 202 and the one substantially properly oriented tooth 206, which can, in various embodiments, be filled by a dental implant and attached to an associated prosthetic dental restoration following realignment of the two teeth 202, 206. Alternatively, a pontic (e.g., a fake tooth) may temporarily be built and/or inserted to fill the space while the dental implant is integrating into the bone. Once the implant is ready to receive the final prosthesis, the pontic may be removed and/or replaced with the final restorative prosthesis by attaching the final restorative prosthesis to the implant.

As appreciated by one of ordinary skill in the relevant art, illustrations in the present disclosure showing a limited number of (e.g., one or two) teeth, implants, and/or pontics are shown for clarity and not by way of limitation. That is, the present disclosure is meant to cover repositioning of one or more misaligned teeth and/or placement and/or positioning of one or more dental implants.

Figure 2B:
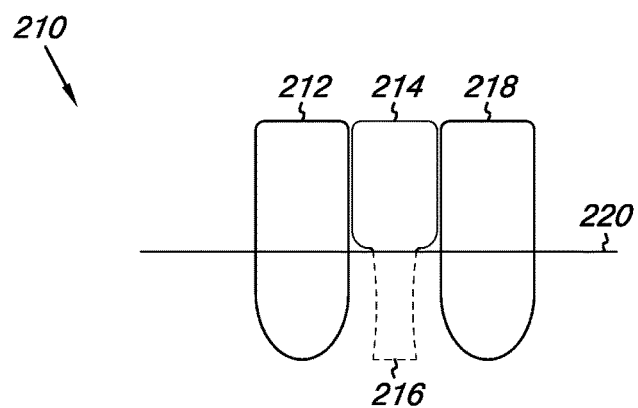
FIG. 2B illustrates an example of aligned teeth in a lower jaw of a patient between which a dental implant has been positioned.

FIG. 2B illustrates an example of aligned teeth in a lower jaw of a patient between which a dental implant has been positioned. The example of aligned teeth 210 illustrated in FIG. 2B shows a first substantially properly oriented tooth 212 adjacent to a prosthetic dental restoration 214 (e.g., a temporary pontic) attached to an implant mount 216, which is adjacent to a second substantially properly oriented tooth 218. The first and second substantially properly oriented teeth 212, 218 are shown to be positioned in a substrate 220 that can, in various embodiments, represent a gum line of a jaw structure.

The example illustrated in FIG. 2B shows that a vacancy between the first and second substantially properly oriented teeth 212, 218 can, in various embodiments, be filled by the prosthetic dental restoration 214 and/or the implant mount 216, for example, following creation of space between the two misaligned teeth 202, 206 illustrated in FIG. 2A. As such, FIG. 2B can, in various embodiments, illustrate a virtual treatment plan incorporating dental treatment, implant placement, and/or a final restoration design.

Figure 2C:
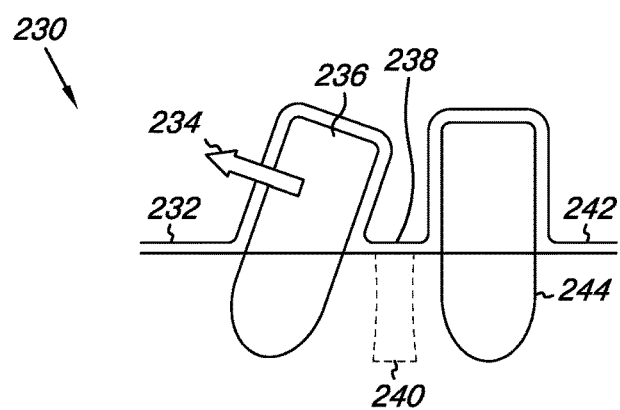
FIG. 2C illustrates a cut away view of an example of a dental positioning adjustment appliance embodiment according to the present disclosure.

FIG. 2C illustrates a cut away view of an example of a dental positioning adjustment appliance embodiment according to the present disclosure. The example of creation of space for positioning an implant 230 illustrated in FIG.

2C shows an embodiment of a dental positioning adjustment appliance 232 (e.g., an aligner) functioning to reposition 234 one improperly oriented tooth 236.

Repositioning the improperly oriented tooth 236 can, in various embodiments, allow creation of space 238 sufficient to insert and/or properly position an implant 240 between the improperly oriented tooth 236 and a substantially properly oriented tooth 244. A portion of the aligner 242 associated with a substantially properly oriented number of teeth can, in various embodiments, serve as an anchor for initially and/or continuously repositioning the improperly oriented tooth 236. The portion of the aligner 242 also can maintain the position of tooth 244 while tooth 236 is being moved.

In various embodiments as described in the present disclosure, an aligner can be designed to include an implant positioning guide. The aligner also can, in various embodiments, include an "offset" portion (e.g., area and/or volume) separating the aligner a distance from the implant and/or surrounding tissue to allow the implant to osseointegrate without occlusal pressure while the remaining dental treatment is being completed. Hence, the implant can be placed while the dental treatment is continuing, rather than at the end of the dental treatment.

The aligner also can be designed to include one or more fake teeth (e.g., pontics) that are temporarily used to aesthetically camouflage the edentulous (i.e., toothless) region while the tissue around the implant is healing. A number of pontics, for example, can be used as temporary "try-ins" to assist in enabling patient satisfaction with planning of tooth shade, shape, and/or position, among other characteristics, prior to placement of a more permanent final restoration. With these features, the implant can be placed while the orthodontic treatment is continuing, rather than at the end of the orthodontic treatment, while aiding in patient satisfaction with appearance during the process.

A dental treatment plan as described in the present disclosure can, in various embodiments, include three-dimensional (3-D) digital scanning of the patient's dentition. This can be accomplished a number of ways, for example, CT scanning, magnetic resonance imaging (MRI) scanning, light scanning, destructive scanning, and/or laser scanning, among other scanning technologies. In some embodiments, the patient's jaw and/or soft tissue structure can be scanned using, for example, CT scanning, and/or MRI scanning, among other scanning technologies.

Hybrid scanning technology also can be used, whereby general anatomical structures are identified using direct patient scanning (e.g., CT and/or MRI) and more accurate surface details are imaged using direct light and/or dental impression/model scans, with the multiple scans merged together via landmark superimposition to create a final working scan. In such embodiments, the 3-D dentition structure scan can be superimposed over the 3-D scan of the patient's jaw and/or soft tissue structure. This can be accomplished using various shape matching algorithms (e.g., AST matching as described in a number of published applications and/or issued patents assigned to Align Technology, Inc.).

A hybrid scan as just described may capture high accuracy surface detail images of the dentition without exposing the patient to unnecessarily high amounts of ionizing radiation. This methodology may also overcome inaccuracy problems associated with radiation scatter that can occur when scanning metal objects, such as dental fillings and/or prostheses containing metal (e.g., dental crowns and/or bridges, among others).

Such a superimposition can result in a high resolution 3-D dentition model matched to the patient's dental roots, tissues, jaw bones, nerves, and/or other soft and hard tissue features (e.g., jaw muscles, tongue, cheek, and/or facial attributes) that can be used as substantially fixed markers. The high resolution 3-D model of the teeth and/or associated structures can be utilized for planning of the final dental alignment and/or occlusion prior to starting treatment. The high resolution 3-D model of the teeth and/or associated structures also can be utilized for planning of implant placement and/or positioning prior to starting treatment.

In some embodiments, virtual final restorations (e.g., including the crowns that are to be placed) can be created to determine favorable and/or desirable positioning of the final prosthesis on top of the implants and/or improve occlusion against teeth of an opposing arch after the dental therapy is completed. Individual virtual teeth can be moved to a number of positions in consideration of the desired implant placement. One or more virtual implants are created and positioned relative to the 3-D fixed markers. The virtual teeth, aligners, virtual implants, and/or virtual restoration may be repositioned in an iterative fashion before settling on a desired dental treatment plan.

Dental movement of improperly oriented and/or positioned teeth can, in various embodiments, be parsed into an incremental treatment plan that animates the progression of the virtual teeth from an initial state to a final state. Each step can be calibrated and/or constrained, for example, based on incremental tooth root movement (e.g., no more than 0.25 millimeter (mm) movement per tooth per step), among other methods. In some embodiments, the increments can be evaluated for interdental digital overlaps called "collisions" and these collisions can be resolved such that the teeth can slide past each other during orthodontic dental treatment.

For each incremental movement of treatment, a dental aligner can, in various embodiments, be formed to enable one or more of the patient's teeth to be moved into a geometry corresponding to an interior topology of the aligner (e.g., see FIG. 1B). Once the positioning of the teeth has substantially conformed to the geometry of a preceding aligner, the next aligner in a series of aligners can be worn for a number of hours or weeks of wear to continue progression of tooth movement to a planned final state, for example, as determined by the virtual final restoration plan.

In some instances, such as with traditional orthodontics, the final position of the implant may not be predetermined and the implant may be placed and/or positioned after the orthodontic treatment is completed. Hence, the patient may have to wait a number of months during orthodontic treatment to, for example, expose the favorable and/or desirable implant location, as well as after orthodontic treatment to allow for adequate healing and osseointegration before the patient can have their implant restored with a crown or other prosthesis. In contrast, as described in the present disclosure, at the earliest stage in the dental treatment where a desired implant location is fully accessible (e.g., when movement has progressed sufficiently that no tooth is obstructing the desired target implant location) and stable (e.g., no other teeth are intended to be moved into the implant space), an implant can, in various embodiments, be placed and/or positioned in the desired location while the orthodontic treatment is continuing.

The final position of the implant can be determined digitally in connection with the dental aligner treatment and, when the necessary space has been created by the orthodontic treatment, the implant can be placed and/or positioned while the orthodontic treatment is continuing. Placing and/or positioning the implant during the orthodontic treatment, as opposed to after the orthodontic treatment, may shorten the overall treatment time because the healing period for osseointegration can simultaneously occur while the remaining orthodontic treatment is continuing.

This can reduce the delay in placement of the final restoration (e.g., a crown) once the dental treatment has been completed. By working in parallel, instead of in series, the patient can have ample time for implant osseointegration, and this may allow for an improved prognosis for the health and longevity of the dental implant and/or the health and/or comfort of the patient.

To facilitate the implant placement and/or positioning process, a virtual object can, in various embodiments, be placed at the final planned stage of treatment to indicate a desired position where the implant should be placed. That is, by simulating the orthodontic treatment, on which the aligner topology (e.g., contours) will be based, the implant position can be predetermined and/or identified with a virtual indicator relative to the virtual dentition, which can be transferred to the contours of the actual aligners. During the treatment planning phase, the virtual teeth representing the actual dentition can be set to a position where the implant could be adequately placed without obstruction from the neighboring teeth and in a manner that avoids important anatomical structures (e.g., nerves, vessels, and such).

This position can, for example, provide the earliest time at which the implant can be placed and/or positioned, for instance, so long as no other teeth cross in the path of the implant for the rest of the dental treatment. For example, additional space (e.g., 2 mm) may be desired to allow for an adequate implant space and the additional space can be created in five months with orthodontic treatment, although the entire orthodontic treatment may require an additional twelve months due to the severity of dental misalignment. In such situations, the implant can, as described in the present disclosure, be placed after five months of treatment, thereby allowing seven months of osseointegration time to occur while the remaining orthodontic treatment is ongoing.

As described in the present disclosure, the virtual indicator representing the desired position of the dental implant (e.g., corresponding to the position where the final restoration is to be placed) can be embodied as a cylinder, space, and/or hole that can, in various embodiments, be built and/or formed into the actual aligner to serve as a guide (e.g., landmark) to assist in correct placement and/or positioning of the implant (e.g., which can show a dentist or implant surgeon where to place the implant). In some embodiments, the landmark can be a simple indicator that, for example, when used in conjunction with the CT image, can direct the dentist or implant surgeon to an appropriate general location for the implant. In some embodiments, the landmark can serve as a precise drill guide to enable the proper angulation and/or depth of the implant to be built into the aligner itself.

This positioning feature can, in various embodiments, enable the dentist or implant surgeon to correctly position the implant in the desired target position in light of the possibility that additional orthodontic treatment may continue after the placement of the implant. That is, the most visually "obvious" position at the time of implant placement, without the landmark, may not in fact be the appropriate position when the orthodontic treatment is completed.

Figure 3A:
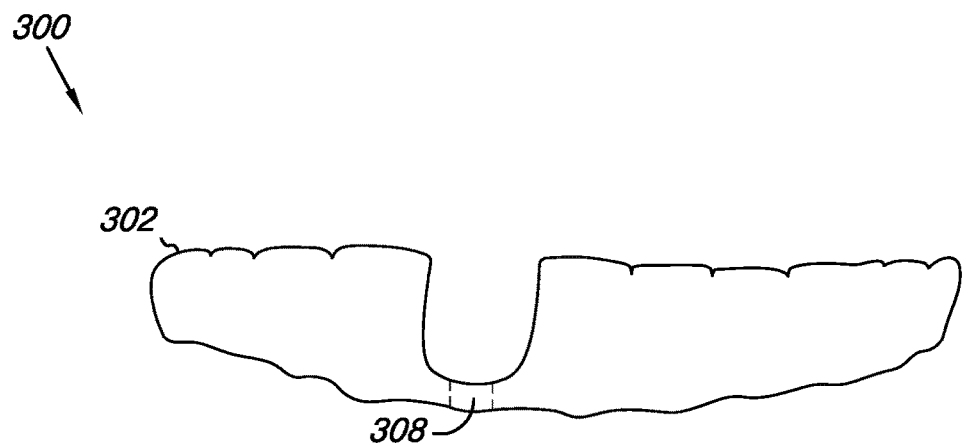
FIGS. 3A-3C illustrate embodiments of dental positioning adjustment appliances usable for dental implant positioning according to the present disclosure.
Figure 3B:
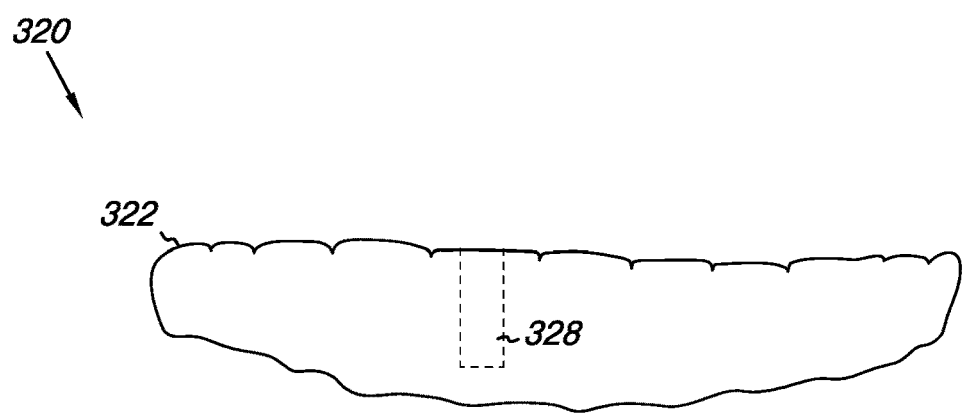
Figure 3C:
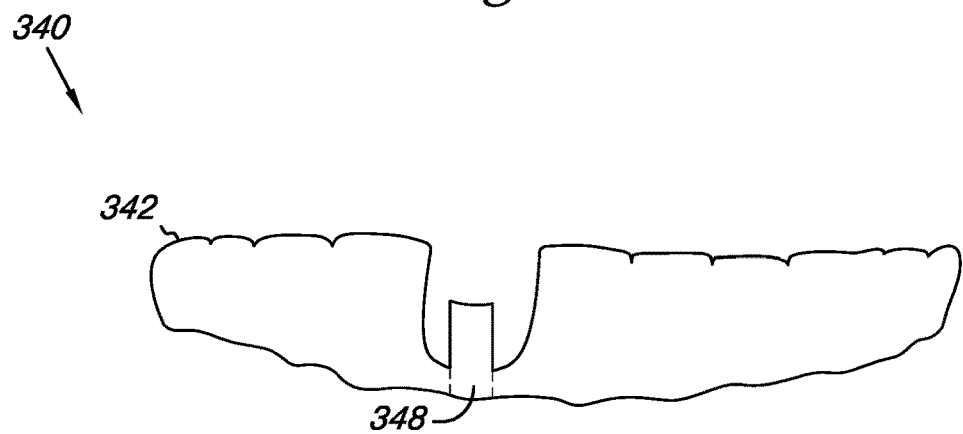

FIGS. 3A-3C illustrate embodiments of dental positioning adjustment appliances usable for dental implant positioning according to the present disclosure. The embodiments of the dental positioning adjustment appliances 300, 320, and 340 illustrated in FIGS. 3A-3C, respectively, show dental aligners formed to include implant placement guides that can, in various embodiments, serve as a landmark for positioning of a dental implant by a dentist or implant surgeon.

FIG. 3A illustrates an example of an embodiment 300 in which the aligner 302 can, in various embodiments, include a perforation 308 (e.g., one or more holes in various shapes through the substance of the aligner). The perforation 308 through the aligner 302 can serve as the implant placement landmark to direct positioning of the implant by a dentist or implant surgeon.

The landmark can, in various embodiments, be used directly as a drill guide, or indirectly as a marking device for a subsequent drill guide. The landmark can, in some embodiments, be used with a separate attachment that serves as a drill guide, whereby the landmark serves, for example, as a receptacle for the attachment.

FIG. 3B illustrates an example of an embodiment 320 in which the aligner 322 can, in various embodiments, include an inset 328 that progresses partially or completely through the substance of the aligner 322 (e.g., one or more insets in various cylindrical or other shapes through the substance of the aligner). The inset 328 illustrated in FIG. 3B can, in some embodiments, be formed as a perforation having longer sides (e.g., a circular wall of a cylinder) than the perforation 308 illustrated in FIG. 3A.

As indicated with regard to FIG. 3A, the landmark illustrated in FIG. 3B can, in various embodiments, be used directly as a drill guide, or indirectly as a marking device for a subsequent drill guide. The landmark can, in some embodiments, be used with a separate attachment that serves as a drill guide, whereby the landmark serves, for example, as a receptacle for the attachment.

The inset 328 illustrated in FIG. 3B can, in various embodiments, be formed in the direction of a desired angulation for the implant. As such, the inset 328 can, in some embodiments, provide wall support to allow tactile feedback for an implant drill, thereby serving as the implant placement guide to direct positioning of the implant by a dentist or implant surgeon. When used as a separate attachment that serves as the guide, the angle of the walls of the guide can correctly position the separate attachment relative to the surrounding teeth and/or oral structures.

FIG. 3C illustrates an example of an embodiment 340 in which the aligner 342 can include an everted cylinder 348 that, in various embodiments, can include a top end of the everted cylinder 348 positioned a fixed distance from a bottom end of the everted cylinder 348 (e.g., one or more everted cylinders in various shapes and/or lengths). The everted cylinder 348 illustrated in FIG. 3C can, in various embodiments, be formed in the direction of a desired angulation for the implant.

Similar to the inset 328 illustrated in FIG. 3B, the everted cylinder 348 illustrated in FIG. 3C can, in various embodiments, provide wall support to allow tactile feedback for the implant drill. Additionally, the everted cylinder 348 can, in various embodiments, allow a drill bit of the implant drill to line up with a wall of the everted cylinder 348 and allow a base of the implant drill to be stopped by the top end of the everted cylinder 348 so that the implant drill bit progresses only a predetermined distance into, for example, the jaw bone of the patient.

That is, the base of the implant drill can be prevented from passing a contact point with the top end of the everted cylinder 348. When the drill guide is a separate attachment, the attachment can, in various embodiments, be coupled to the everted cylinder.

The everted cylinder 348 can, in some embodiments, provide tactile feedback to guide the direction and/or depth of the implant drill, thereby serving as the implant placement guide to direct positioning of the implant by a dentist or implant surgeon. As such, as described with regard to FIGS. 3A-3C, a landmark can be selected from a group that includes a depression, a marking, a hole, a fixture, an inset, and/or a drill guide structure (e.g., an everted cylinder), among other landmark configurations for either direct or indirect guidance for the implant placement.

Figure 4A:
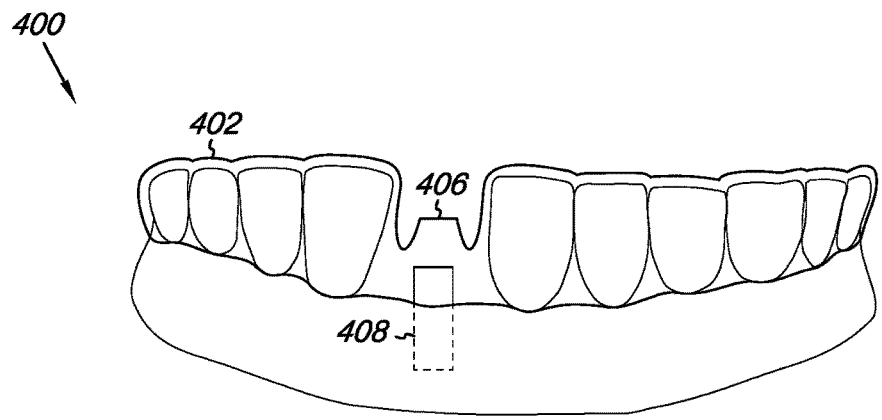
FIGS. 4A-4E illustrate further embodiments of dental positioning adjustment appliances usable for dental implant positioning according to the present disclosure.
Figure 4B:
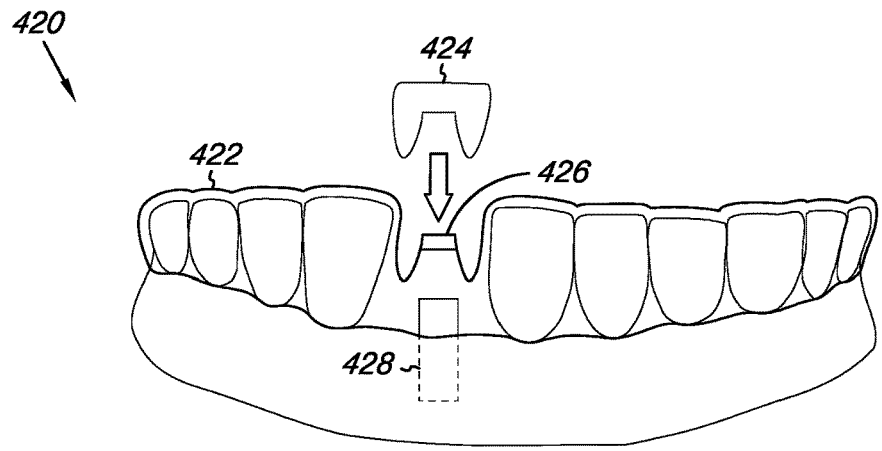
Figure 4C:
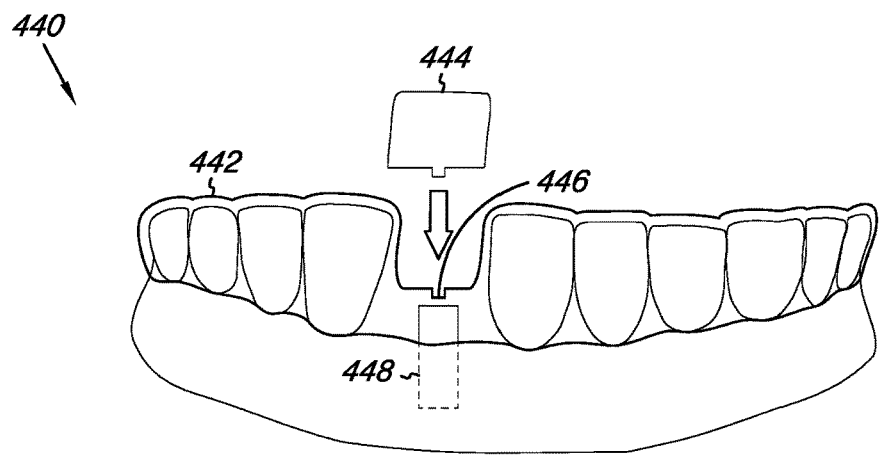

FIGS. 4A-4C illustrate further embodiments of dental positioning adjustment appliances usable for dental implant positioning according to the present disclosure. After an implant has been placed and/or positioned, a dental positioning adjustment appliance (e.g., an aligner) can be applied that is formed with an offset (e.g., relief) portion.

The offset portion can, in various embodiments, be provided in the aligner so that the aligner does not press on the tissue surrounding the implant. The offset portion can, in various embodiments, be built into the aligner. The three embodiments of the dental positioning adjustment appliances 400, 420, and 440 illustrated in FIGS. 4A-4C, respectively, show dental aligners formed to include offset portions, in various embodiments, although other configurations are covered by the present disclosure.

FIG. 4A illustrates an example of an embodiment 400 in which the aligner 402 can, in various embodiments, include an offset portion 406 (e.g., one or more offset portions in various shapes formed in the substance of the aligner). The offset portion 406 of the aligner 402 can serve to reduce pressure from parts of the aligner 402 on an implant 408 (which can, in various embodiments, include a healing abutment and/or cap) and/or on tissue surrounding the implant.

In many instances, placement of a tooth-like object (e.g., a pontic) on, or creation of a tooth-like object as part of, the aligner may be desirable (e.g., for aesthetic reasons) in combination with the offset feature. In various embodiments, the tooth-like object can be secured as part of the aligner, for example, by forming the aligner and tooth-like object together, by using a geometry built into the aligner as a mating fit to the tooth-like object with a locking mechanism that fits the geometry of the tooth-like object, by designing a tooth-shaped bubble to allow tooth-colored material to be placed into the tooth-shaped bubble, and/or by using a rivet-like system to allow a tooth-like object to be physically snapped onto the aligner without using adhesive substances, among other arrangements.

FIG. 4B illustrates an example of an embodiment 420 in which the aligner 422 can, in various embodiments, include an offset portion (e.g., the offset portion 406 as illustrated in FIG. 4A) to reduce pressure from parts of the aligner 422 on an implant 428 and/or on tissue surrounding the implant. The aligner 422 illustrated in FIG. 4B shows that the aligner 422 can include an abutment geometry 426, in various embodiments, that can enable attachment (e.g., with an adhesive substance, a mechanical connection, etc.) of a tooth-like object 424 (e.g., a pontic) to the abutment geometry 426 and, consequently, to the aligner 422. As such, FIG. 4B illustrates that an aligner can, in various embodiments, be formed with an offset portion and an abutment associated with the offset portion, which can enable attaching, for example, a pontic to the abutment.

FIG. 4C illustrates an example of an embodiment 440 in which the aligner 442 can, in various embodiments, include an offset portion (e.g., the offset portion 406 as illustrated in FIG. 4A) to reduce pressure from parts of the aligner 442 on an implant 448 and/or on tissue surrounding the implant. The aligner 442 illustrated in FIG. 4C shows that the aligner 442 can be formed such that a tooth-like object 444 (e.g., a pontic) can, in various embodiments, be attached to an abutment geometry 446 with a rivet-like connection.

That is, in some embodiments, the tooth-like object 444 can be attached to the abutment 446 without using an adhesive substance. As such, FIG. 4C illustrates that an aligner can, in various embodiments, be formed with an offset portion and an abutment associated with the offset portion, which can enable a rivet-like connection to attach, for example, a pontic to the abutment.

Figure 4D:
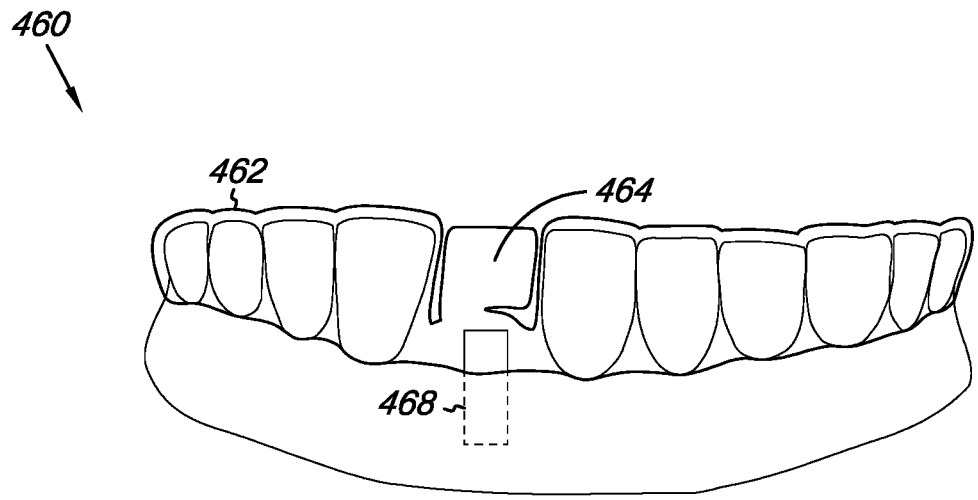

FIG. 4D illustrates an example of an embodiment 460 in which the aligner 462 can, in various embodiments, include an offset portion (e.g., the offset portion 406 as illustrated in FIG. 4A) to reduce pressure from parts of the aligner 462 on an implant 468 and/or on tissue surrounding the implant. The aligner 462 illustrated in FIG. 4D shows that the aligner 462 can be formed such that a tooth-like object 464 (e.g., a pontic) can, in various embodiments, be built into and/or formed as part of the aligner 462.

That is, in various embodiments, both the tooth-like object 464 and the offset can be built into and/or formed from the polymeric material from which the rest of the aligner 462 is formed, although the present disclosure is not limited to using the same material for the tooth-like object 464 and the aligner 462. In some embodiments, the tooth-like object 464 can be formed as a shell of the polymeric material or other suitable material.

In some embodiments, as illustrated in FIG. 4D, the tooth-like object 464 can, in various embodiments, have a notch (or another appropriate weakened arrangement) formed therein to facilitate removal of the tooth-like object 464 in order to access the implant 468 through the offset area or otherwise. As such, FIG. 4C illustrates that an aligner can, in various embodiments, be formed with an offset portion and a tooth-like object associated with the offset portion, which can enable forming the aligner, the offset portion, and the tooth-like object as a single construct.

Figure 4E:
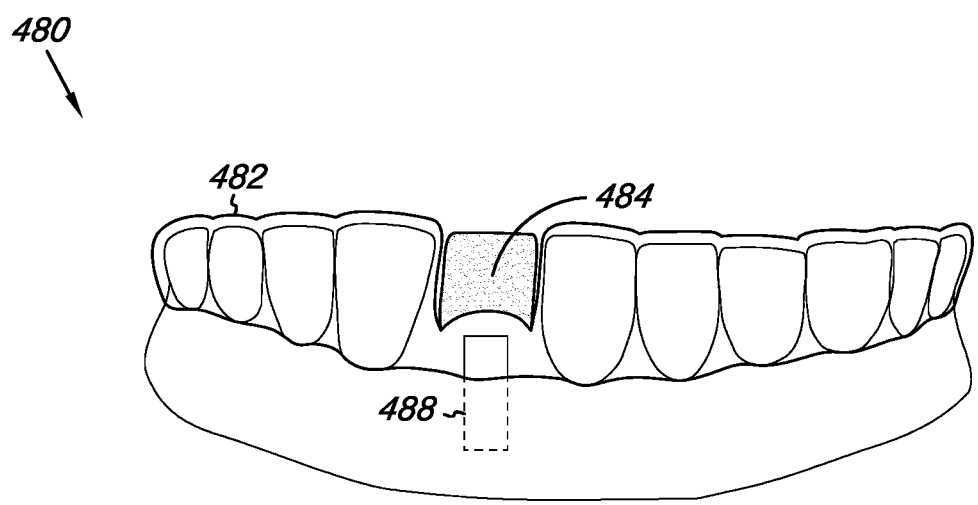

FIG. 4E illustrates an example of an embodiment 480 in which the aligner 482 can, in various embodiments, include an offset portion (e.g., the offset portion 406 as illustrated in FIG. 4A) to reduce pressure from parts of the aligner 482 on an implant 488 and/or on tissue surrounding the implant. The aligner 482 illustrated in FIG. 4E shows that the aligner 482 can be formed such that a tooth-like object 484 (e.g., a pontic) can, in various embodiments, be built into and/or formed as part of the aligner 482, similar to the embodiment 460 illustrated in FIG. 4D.

The embodiment 480 illustrated in FIG. 4E can, in various embodiments, differ from the embodiment 460 in that a portion of the shell can be filled with a solid material (e.g., the polymeric material from which the aligner 482 is formed or otherwise) to make the tooth-like object 484 more substantially solid. In various embodiments, the shell of the tooth-like object 484 can be partially or completely filled with the solid material as long as an offset portion is preserved (e.g., the base of the solid material in the shell becomes the top of the offset portion).

As described with regard to FIG. 4D, both the tooth-like object 484 and the offset illustrated in FIG. 4E can, in various embodiments, be built into and/or formed from the polymeric material from which the rest of the aligner 482 is formed, although the present disclosure is not limited to using the same material for the tooth-like object 484 and the aligner 482. In some embodiments, the tooth-like object 484 can be formed as a shell and/or filler of the polymeric material or other suitable material.

In some embodiments, the tooth-like object, as illustrated in FIGS. 4D and 4E, can be a pontic, in various embodiments, that is built and/or formed from a tooth library and/or a "copy and paste" from another tooth, as will be appreciated by one of ordinary skill in the relevant art. As also will be appreciated by one of ordinary skill in the relevant art, configurations of the embodiments of the aligners, offsets, implants, and/or tooth-like objects illustrated in FIGS. 4A through 4E are simplified for purposes of clarity and are not to be construed as limitations thereof unless explicitly stated as such. For example, the thickness of a layer of polymeric material in an aligner can vary depending upon the positioning and/or application thereof, although such thickness may be represented by a uniformly thin line in FIGS. 4A through 4C.

As will further be appreciated by one of ordinary skill in the relevant art, various features are grouped together in the description of the present disclosure in a single embodiment for the purpose of streamlining the disclosure. This method of disclosure, however, is not to be interpreted as reflecting an intention that the embodiments of the disclosure require more features than are expressly recited in each of the following claims. Rather, as the claim recitations reflect, inventive subject matter lies in less than all features of a single disclosed embodiment.

Hence, predetermining a treatment plan with a virtual model as described in the present disclosure may be a recommended and claimed methodology, however, just forming and/or using an aligner as described in the disclosure and as recited in the following claims is intended as novel subject matter to be protected. For example, novel subject matter as described in the present disclosure can be included in a portion of an aligner, rather than the whole aligner, and remain consistent with the teachings of the present disclosure.

Accordingly, a series of removable dental positioning appliances, as described in the present disclosure, can include, in various embodiments, a first number of aligners for repositioning one or more teeth from a first configuration to a second configuration, and a second number of aligners to reposition one or more teeth from the second configuration to a successive configuration. The repositioning of the one or more teeth to the second configuration can, in various embodiments, expose an implant location space. For example, a series of multiple aligners may be necessary to achieve a desired alignment endpoint configuration. However, the desired alignment endpoint configuration can be planned in the beginning at or near the same point in time as an intermediate alignment configuration (e.g., the second configuration) that allows appropriate implant positioning.

The treatment plan can be revisited, for example, at or near each point in time when an intermediate aligner in the series of aligners is replaced by a successive aligner and altered, if desired, depending upon a level of success achieved. For example, the desired endpoint configuration may be to have a 9 mm width spacing for a single implant. After a succession of 10 aligners, the progress toward the desired endpoint spacing can be measured and, in some instances, another 10 aligners may be prescribed.

After the second 10 aligners have been utilized, progress can be measured again to determine whether the original desired target of 9 mm is realistically attainable. If so, and when necessary, more aligners can be prescribed until the desired spacing is achieved. If the desired spacing of 9 mm appears not to be realistically attainable, an alternative desired spacing can be determined.

The concept of determining an implant position based upon a future position of teeth resulting from orthodontic treatment can be implemented at any point in the series of aligners. That is, when an adequate implant space is achieved, the implant can be placed and/or positioned, even though additional orthodontic treatment is still planned for execution.

In some embodiments, the series of removable dental positioning appliances can, in various embodiments, include one or more aligners including an offset area corresponding to some portion (e.g., area) of the implant location space. In some embodiments, the second number of aligners can, in various embodiments, be configured with either an abutment geometry for attaching a temporary tooth structure in the offset area or a pontic geometry built into the offset area.

In some embodiments, the series of removable dental positioning appliances can, in various embodiments, include successive configurations based on an optimal dental occlusion including a predetermined implant location space. In some embodiments, the series of removable dental positioning appliances can, in various embodiments, include at least one aligner corresponding to the second configuration that can include a guide for implant placement within the implant location space. A configuration for the guide can be, for example, a depression, a marking, a hole, a fixture, an inset, a drill guide mating feature, and/or a drill depth and alignment guide structure, among other configurations.

Accordingly, as described in the present disclosure, a series of dental positioning appliances can be used to expose one or more positions for one or more implants. In various embodiments, a first number of aligners can be used to reposition one or more teeth from a first configuration to a second configuration.

In such embodiments, the one or more teeth that are repositioned to the second configuration expose at least one implant location space. A number of implants can then be placed in the exposed one or more implant location spaces. In some such embodiments, a second number of the series of dental appliances can be used to reposition one or more teeth from the second orientation to a successive orientation.

As described in the present disclosure, at least one of the first number of aligners can include at least one landmark to serve as a guide for placement of an implant. In various embodiments, landmarks can be formed in aligners as one or more of, for example, a depression, a marking, a hole, a fixture, an inset, and/or a drill guide structure in the aligner, among other suitable structures.

In some embodiments, at least one of the second number of aligners can include an offset area corresponding to some portion of the implant location space. At least one of the second number of aligners also can, in various embodiments, include either an abutment geometry to enable attachment of a temporary tooth structure in the offset area and/or a pontic geometry built into the offset area. In some embodiments, the temporary tooth structure attachable in the offset area or the pontic geometry built into the offset area can be at least partially formed from tooth-colored material.

Figure 5:
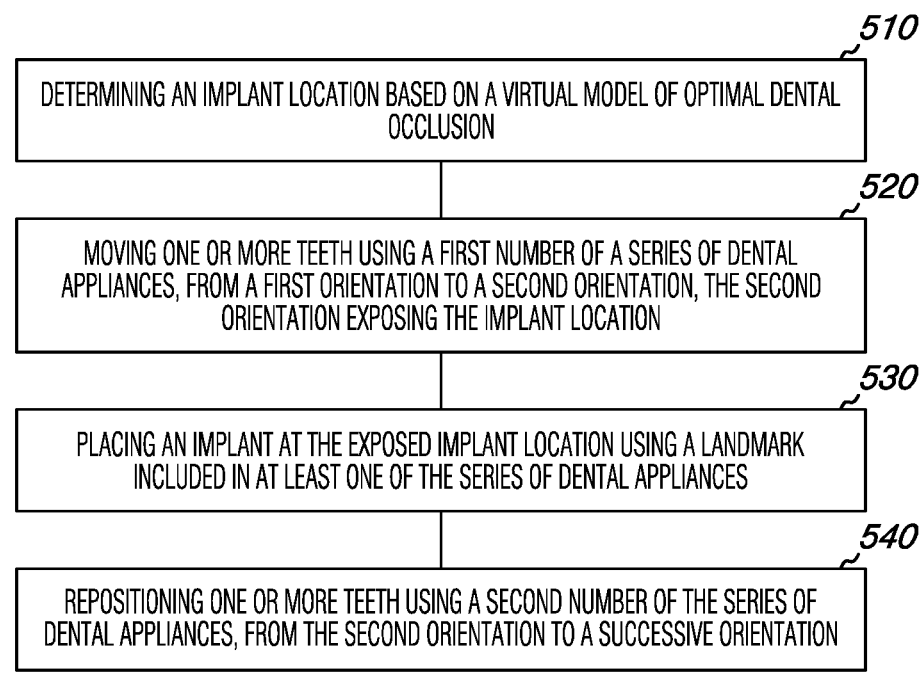
FIG. 5 is a block diagram illustrating a method for positioning an implant with dental treatment according to the present disclosure.

FIG. 5 is a block diagram illustrating a method for positioning an implant with dental treatment according to the present disclosure. Unless explicitly stated, the method embodiments described herein are not constrained to a particular order or sequence. Additionally, some of the described method embodiments, or elements thereof, can occur or be performed at the same, or at least substantially the same, point in time.

The embodiment illustrated in FIG. 5 includes determining an implant location based on a virtual model of an optimized dental occlusion, as shown in block 510. As used in the present disclosure, "optimized dental occlusion" denotes a dental occlusion determined to be favorable and/or desirable by a treatment professional (e.g., a dentist or implant surgeon) with reference to, in some embodiments, a virtual model of dental occlusion that can be either static or dynamic (e.g., that simulates articulation). A dental treatment plan as described in the present disclosure can, in various embodiments, determine the implant location based on the virtual model of optimal dental occlusion through use of 3-D digital scanning of the patient's dentition.

The 3-D digital scanning can be accomplished a number of ways, for example, CT scanning, MRI scanning, light scanning, destructive scanning, and/or laser scanning, among other scanning technologies. In some embodiments, the patient's jaw and/or soft tissue structure can be scanned using, for example, CT scanning, and/or MRI scanning, among other scanning technologies.

In various embodiments, the scanning can include scanning in three dimensions a patient's initial dental anatomy, creating the virtual model of desired dental occlusion based on the patient's dental anatomy, and designing a series of dental appliances (e.g., aligners) where the first orientation is an occlusion of the initial dental anatomy, and the successive orientation is a desired dental occlusion. In some embodiments, the scanning can include digitally scanning a patient's dentition, digitally scanning a dental structure including anatomical features affecting the implant location, and superimposing the dental structure to the dentition of the 3-D patient scan.

As described in the present disclosure, some embodiments of a plan for dental treatment with implant can include creating a virtual model of a number of physical teeth and at least one implant as a virtual tooth, and planning a virtual treatment process including one or more treatments having a number of orientations of the number of virtual teeth. As described herein, the virtual treatment process can include moving at least one of the number of physical teeth to clear an implant location for an optimal dental occlusion configuration.

The virtual treatment process can include placing an implant at the implant location once cleared of physical teeth. Additionally, the virtual treatment process can include positioning at least one of the number of physical teeth outside of the implant location to the optimal dental occlusion configuration while the implant location is healing.

In some embodiments, the virtual treatment process can include fabricating (e.g., forming) a removable dental positioning appliance (e.g., aligner) to implement each increment of the treatment. In various embodiments, the implant location (e.g., a landmark) can be incorporated into one or more of the removable dental positioning appliances.

Block 520 of FIG. 5 shows that one or more teeth can, in various embodiments, be moved (e.g., repositioned) using a first number of a series of dental appliances, from a first orientation to a second orientation, the second orientation exposing the implant location. For example, the implant location that is exposed by moving the one or more teeth to the second orientation can be the implant location determined based upon the virtual model, as described herein.

An implant can be placed at the exposed implant location using a landmark included in at least one of the series of dental appliances (e.g., aligners), as shown in block 530. In some embodiments, the landmark can be a simple indicator that, for example, when used in conjunction with the CT image, can direct the dentist or implant surgeon to an appropriate location for the implant. In some embodiments, the landmark can perforate the dental appliance and serve as a drill guide, or serve as an attachment for a separate drill guide, to enable determination of the angulation and/or depth of the implant to be built into the aligner itself.

In some embodiments, a layer of polymeric material at the site of the landmark may be thin, for example, such that attaching the separate drill guide can assist in providing a guide that reliably enables determination of the angulation and/or depth of the implant. Among various embodiments, the separate drill guide can, in some embodiments, be a cylinder with a circumferential groove forming part of a drill guide mating feature to receive, for example, an edge of a depression, a marking, a hole, a fixture, and/or an inset serving as a landmark.

As shown in block 540, one or more teeth can be repositioned using a second number of the series of dental appliances (e.g., aligners), from the second orientation to a successive orientation. That is, in some embodiments, after placing and/or positioning the implant at the desired location, the first of the second number of the series of aligners can be applied to the patient's teeth to continue repositioning of the teeth from the orientation in which the implant was placed and/or positioned to continue movement of the teeth to a final position.

In some embodiments of the present disclosure, the implant can be placed and/or positioned at the earliest exposing of the implant location. A dental appliance providing an earliest exposing of the implant location can include the landmark, in various embodiments, providing a guide for locating a position for the implant.

As described in the present disclosure, one or more teeth can be repositioned using the second number of the series of dental appliances while the patient is healing from implant placement. In some embodiments, the second number of the series of dental appliances can, in various embodiments, include an offset area corresponding to the implant. By including the offset area in a portion of at least one of the second number of the series of dental appliances, pressure on the location of the implant and/or surrounding tissue can be relieved in order to facilitate healing and osseointegration and/or improved recovery (e.g., reducing impaction trauma to the wound site).

In some embodiments, the second number of the series of dental appliances can, in various embodiments, be configured to have an abutment geometry for attaching a temporary tooth structure in the offset area. Hence, in some embodiments, the temporary tooth structure can, in various embodiments, be attached to the abutment geometry of one or more of the second number of the series of dental appliances.

In some embodiments, the offset area (e.g., included in at least one of the second number of the series of dental appliances) can, in various embodiments, be filled, lined, painted, or coated with tooth-colored material. A dental plan, as described in the present disclosure, can include restoring a tooth structure to the implant once the implant has osseointegrate and the neighboring teeth are repositioned to the desired dental occlusion arrangement. When the space created by the aligner is larger than the intended restoration shape at the implant site and the implant is integrated into the bone, the restoration can be placed as soon as the neighboring teeth have reached a stable position, even if additional orthodontic treatment is still to be preformed elsewhere in the patient's mouth.

Figure 6A:
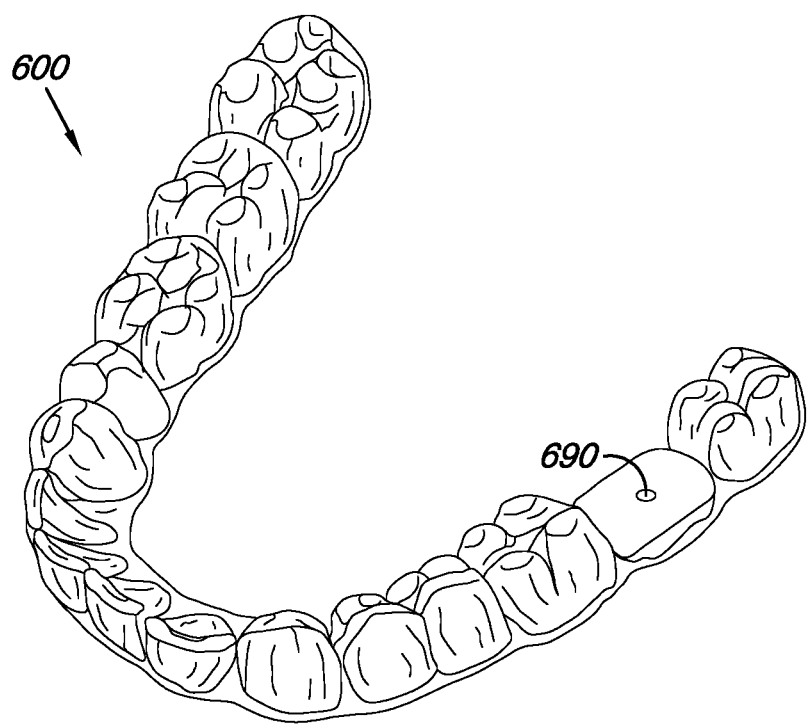
FIG. 6A illustrates a dental positioning adjustment appliance having an aperture for indicating an implant position according to an embodiment of the present disclosure.

FIG. 6A illustrates a dental positioning adjustment appliance having an aperture for indicating an implant position according to an embodiment of the present disclosure. In the embodiment of FIG. 6A, an appliance 600 includes an implant positioning indicator. In the embodiment of FIG. 6A, the indicator (e.g., a landmark) is an aperture 690 provided in the material used to form the appliance. Such apertures can be formed during fabrication of the appliance and/or after the fabrication is complete.

A treatment professional can, for example, view the area through the aperture to see whether the position of the aperture is in the correct anatomical location, and whether there will be enough room for the implant, among other suitable functions. The aperture can be of any suitable size and/or shape. In some embodiments, the aperture can be used to guide the placement of the implant in the indicated location through the aperture.

Additionally, as illustrated in the embodiment of FIG. 6A, the aperture 690 can be placed on a portion of the appliance that is flat. The appliance can have any suitable shape, such as a model tooth contour, a model or actual gum contour, and/or other suitable shapes.

In some embodiments, the appliance 600 can be used to anchor another type of indicator to be placed near the area in which the implant is to be positioned. For example, the indicator can be a wire measuring or pointing device or other type of pointing device that can be utilized to point to the area in which the implant is to be positioned or can be used to help provide measurement information to aid in positioning the implant.

Indicators may, for example, be a self-adhesive indicator, a clip-on indicator, a suction adhered indicator, a bonded indicator, a Velcro-affixed, or a snap-on indicator. However, the embodiments of the present disclosure should not be limited to such methods of attachment.

A wire or other radiopaque material can be beneficial, for example, because it can be viewed in an x-ray. However, the embodiments of the present disclosure should not be limited to such materials.

Figure 6B:
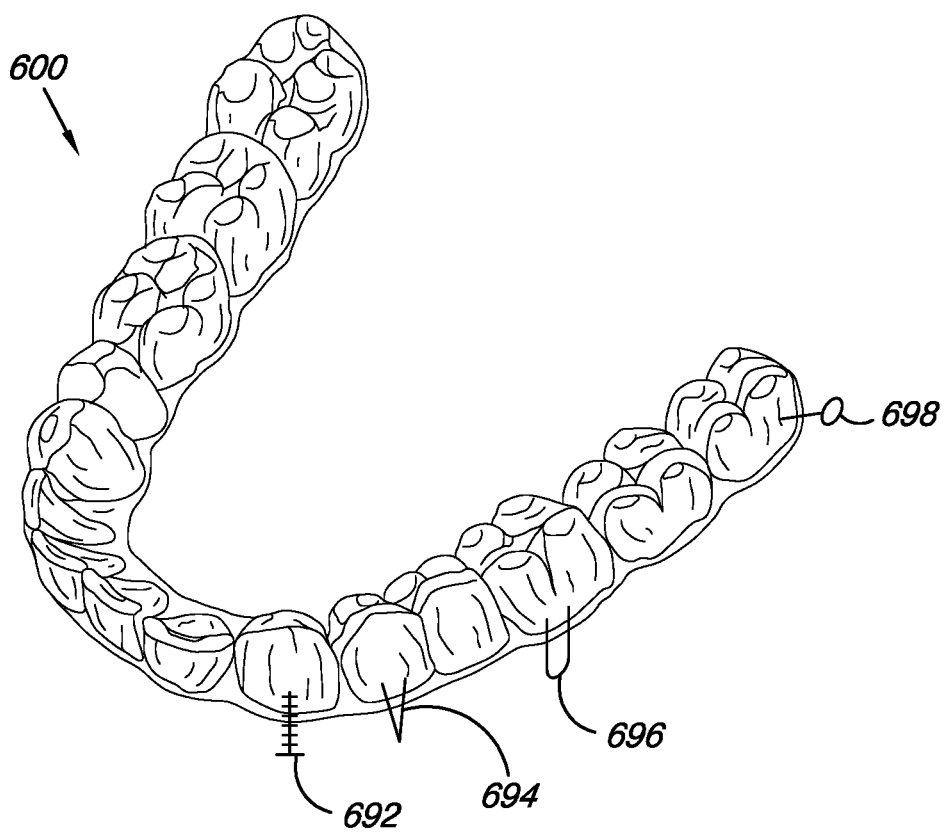
FIG. 6B illustrates a dental positioning adjustment appliance having a number of indicators positioned thereon according to an embodiment of the present disclosure.

FIG. 6B illustrates a dental positioning adjustment appliance having a number of indicators positioned thereon according to an embodiment of the present disclosure. Such indicators can be used for a variety of purposes. For example, such indicators can be used to identify to the clinician where to position an implant, or as a reference from which to determine where to place the implant.

The indicator may also contain a temporary ink or dye that, in some embodiments, can be transferred to the gum tissue to enable the clinician to visualize the desired location of the implant placement, or as a reference position indicator. Such indicators may be particularly useful for the placement of temporary anchorage devices (mini-implants), for example.

In the embodiment illustrated in FIG. 6B, for instance, several indicators are provided. Such indicators can be used as pointing devices that point to the area at which an implant is to be positioned.

Any suitable pointing device can be used in such embodiments. For example, suitable pointing devices can have various shapes and/or sizes, can be made from various materials, and/or can be visible on x-rays and/or via other scanning or photographing techniques, etc.

The indicators can also be placed proximally to (e.g., next to or attached to) the appliance in any suitable manner. A releasable adhesive is one such suitable manner for attachment and allows the indicator to be removed which may be beneficial in some embodiments.

In the embodiment of FIG. 6B, the appliance 600 includes indicators 692, 694, 696, and 698. Such indicators can provide different benefits based upon their shapes.

Such indicators may also contain rotating/pivot joints such that the position can be adjusted and/or locked, for example, while the desired position is being verified with radiographs. In some embodiments, there may also be telescoping or locking telescopic indicators to allow extension of the indicator to more easily locate the desire position, among other benefits.

For example, indicator 692 has a number of different points that can be used as reference such as the left end of the second line from the bottom. This can be helpful in pointing a more exact position.

Indicators 694, a pointer, and 696, a u shape, can provide a general directional orientation (e.g., a vertical versus horizontal alignment to provide that the implant can fit into the area for the implant when installed. Indicator 698 is a circle and as shown, can be used with a reference line.

The circle, for example, can allow for the treatment profession to locate where on the gingiva an implant may be positioned. Such embodiments can, for example be utilized where the clinician can affix the indicator to identify the desired position, mark the tissue through the loop, and then position the implant at the mark. In some embodiments, the implant can be placed directly through the loop. When used with a line, the line can be used to aid in correctly orienting the implant, among other uses for such a feature.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the use of the terms "a", "an", one or more", "a number of", or at least one" are all to be interpreted as meaning one or more of an item is present. Additionally, it is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. An appliance, comprising:
   a plurality of cavities shaped to receive and reposition one or more teeth in a dentition from a first arrangement to a second arrangement different than the first arrangement, the dentition including a vacancy due to one or more misaligned teeth;
   an implant-receiving region adjacent to at least one of the plurality of cavities and shaped to be positioned in the vacancy of the dentition, the implant-receiving region configured to cooperate with the plurality of cavities to adjust a shape of the vacancy for accepting a dental implant;

a radiopaque indicator configured to direct placement of the dental implant into the vacancy of the dentition; and an attachment mechanism to attach the radiopaque indicator to the appliance.

2. The appliance of claim 1, wherein the attachment mechanism comprises one or more of:
- a self-adhesive;
- a curable adhesive;
- a snapping mechanism;
- a hook and loop mechanism;
- a suction mechanism; and
- a clip-on mechanism.

3. The appliance of claim 1, wherein the radiopaque indicator includes a marking device that marks an area of tissue to identify to a clinician a desired position to place the dental implant.

4. The appliance of claim 1, wherein the radiopaque indicator includes a feature to facilitate identifying a tissue area for a clinician to identify a desired position to place the dental implant.

5. The appliance of claim 1, wherein the attachment mechanism is releasable to allow adjustment of the positioning of the radiopaque indicator.

6. The appliance of claim 5, wherein the radiopaque indicator includes a locking mechanism to lock the radiopaque indicator in an adjusted position after adjustment of the positioning in order to verify the adjusted position for placement of the dental implant.

7. The appliance of claim 1, wherein a length dimension of the radiopaque indicator is adjustable.

8. The appliance of claim 7, wherein the radiopaque indicator includes a locking mechanism for locking the length dimension to secure the radiopaque indicator for placement of the dental implant.

9. The appliance of claim 1, wherein at least a portion of the radiopaque indicator is telescopic.

10. The appliance of claim 1, wherein the radiopaque indicator comprises a pointing device, an aperture, or a surgical guide configured to direct placement of the dental implant.

11. The appliance of claim 1, wherein the implant-receiving region comprises an open space adjacent to the at least one of the plurality of cavities.

12. The appliance of claim 1, wherein the implant-receiving region is configured to adjust a position of one or more teeth away from the vacancy.

13. The appliance of claim 1, wherein the implant-receiving region comprises an artificial tooth.

14. The appliance of claim 1, wherein the radiopaque indicator is attached to the implant-receiving region.

15. A method of adjusting a dentition for a dental implant, comprising:
sequentially placing a number of dental appliances to the dentition according to a treatment plan, wherein each of the dental appliances comprises a plurality of cavities shaped to receive and reposition one or more teeth of the dentition from a first configuration to a second configuration different than the first configuration, wherein the dentition includes a vacancy due to one or more misaligned teeth, at least one dental appliance including an implant-receiving region adjacent to at least one of the plurality of cavities and shaped to be positioned in the vacancy of the dentition, the implant-receiving region configured to cooperate with the plurality of cavities to adjust a shape of the vacancy for accepting the dental implant, wherein the at least one dental appliance includes a radiopaque indicator attached to the at least one dental appliance by an attachment mechanism, the radiopaque indicator configured to direct placement of the dental implant into the vacancy of the dentition.

16. The method of claim 15, wherein:
the indicator includes a number of different lines and end points to provide a reference location for the dental implant; and
wherein the method includes placing the dental implant at the reference location via the number of different lines and end points.

17. The method of claim 15, wherein:
the indicator is a pointer configured to provide a directional orientation for the dental implant; and
wherein the method includes placing the dental implant using the directional orientation via the pointer.

18. The method of claim 15, wherein:
the indicator is a U-shape configured to provide a directional orientation for the dental implant; and
wherein the method includes placing the dental implant using the directional orientation via the U-shape.

19. The method of claim 15, wherein the indicator is a circle and reference line configured to provide a reference location for the dental implant.

20. The method of claim 19, wherein the method includes:
marking an area of tissue at the reference location via the circle to identify to a clinician the reference location to place the dental implant; and
placing the dental implant at the reference location.

21. The method of claim 19, wherein the method includes placing the dental implant through the circle at the reference location.

22. The method of claim 19, wherein the method includes placing the dental implant at the reference location using the reference line.

23. A plurality of dental appliances for repositioning one or more teeth of a dentition, the plurality of dental appliances comprising:
at least one dental appliance including:
a plurality of cavities shaped to receive and reposition the one or more teeth in the dentition from a first arrangement to a second arrangement different than the first arrangement, the dentition including a vacancy due to one or more misaligned teeth;
an implant-receiving region adjacent to the at least one of the plurality of cavities and shaped to be positioned in the vacancy of the dentition, the implant-receiving configured to cooperate with the plurality of cavities to adjust a shape of the vacancy for accepting a dental implant;
a radiopaque indicator attached to the implant-receiving region, the radiopaque indicator configured to direct placement of the dental implant into the vacancy of the dentition; and
an attachment mechanism to attach the radiopaque indicator to the at least one dental appliance.

24. The plurality dental appliances of claim 23, wherein:
the radiopaque indicator includes at least one of a rotating joint and pivoting joint; and
wherein the at least one rotating joint and pivoting joint is configured to adjust the radiopaque indicator to a reference location for placement of the dental implant.

25. The plurality dental appliances of claim 23, wherein:
the radiopaque indicator includes at least one of a telescoping and locking telescoping mechanism; and
wherein the at least one of the telescoping and locking telescoping mechanism is configured to adjust the radiopaque indicator to a reference location for placement of the dental implant.

26. The plurality of dental appliances of claim 23, wherein the radiopaque indicator comprises a pointing device, an aperture, or a surgical guide configured to direct placement of the dental implant.

27. The plurality of dental appliances of claim 23, wherein the implant-receiving region comprises an open space adjacent to the at least one of the plurality of cavities.

* * * * *